(12) United States Patent
Chang et al.

(10) Patent No.: US 6,803,360 B1
(45) Date of Patent: Oct. 12, 2004

(54) COMPOSITIONS AND METHODS FOR REDUCING RADIATION AND DRUG RESISTANCE IN CELLS

(75) Inventors: Esther H. Chang, Chevy Chase, MD (US); Kathleen F. Pirollo, Rockville, MD (US)

(73) Assignee: Georgetown University, Washington, DC (US)

( * ) Notice: Subject to any disclaimer, the term of this patent is extended or adjusted under 35 U.S.C. 154(b) by 115 days.

(21) Appl. No.: 09/716,320

(22) Filed: Nov. 21, 2000

Related U.S. Application Data

(63) Continuation-in-part of application No. 09/480,143, filed on Jan. 10, 2000, now abandoned, which is a continuation-in-part of application No. 09/601,444, filed on Jan. 4, 2001, now Pat. No. 6,749,863, and a continuation of application No. 08/991,830, filed on Dec. 16, 1997, now Pat. No. 6,027,892.

(60) Provisional application No. 60/083,175, filed on Apr. 27, 1998, provisional application No. 60/066,188, filed on Nov. 19, 1997, and provisional application No. 60/034,160, filed on Dec. 30, 1996.

(51) Int. Cl.[7] .......................... A01N 43/04; C12Q 1/68; C12N 15/88; C07H 21/02; C07H 21/04
(52) U.S. Cl. ........................ 514/44; 435/6; 435/91.1; 435/91.31; 435/458; 536/23.1; 536/24.5
(58) Field of Search ...................... 435/6, 91.1, 91.31, 435/455, 458, 325, 366, 375; 536/23.1, 24.5, 24.31, 24.33; 514/44

(56) References Cited

U.S. PATENT DOCUMENTS

| | | |
|---|---|---|
| 5,576,208 A | 11/1996 | Monia et al. |
| 5,599,704 A | 2/1997 | Thompson et al. |
| 5,734,039 A | 3/1998 | Calabretta et al. |
| 6,027,892 A | 2/2000 | Chang et al. |

FOREIGN PATENT DOCUMENTS

| | | |
|---|---|---|
| WO | WO 94/15645 | 7/1994 |
| WO | WO 95/32987 | 12/1995 |
| WO | WO 97/10007 | 3/1997 |
| WO | WO 97/28817 | 8/1997 |

OTHER PUBLICATIONS

Jen et al. Stem Cells, vol. 18, 2000, pp. 307–319.*
Ma et al. Biotechnology Annual Review, vol. 5, Jul. 19, 2000, pp. 155–196.*
Branch, TIBS 23, pp. 45–50, Feb. 1998.*
Flanagan et al., Nature Biotechnology, vol. 17, No. 1, pp. 48–52, Jan. 1999.*
Blackshear, Toxicologic Pathology, vol. 29, No. 1, pp. 105–116, 2001.*
Sigmund, Thromb. Vasc. Biol., vol. 20, pp. 1425–1429, 2000.*
Chirila et al., Biomaterials, vol. 23, pp. 321–342, 2002.*
Fritz et al. J. of Colloid and Interface Science, vol. 195, pp. 272–288, 1997.*
Adams, M.D. et al. Nature vol. 377, Supp., pp. 3–17 (1995).*
Bennett et al., Chapter 2 from Methods in Molecular Medicine: Antisense Therapeutics (ed. Agrawal), Humana. Press Inc. Totowa, N.J., 1996, pp. 13–46.*
Agrawal et al. Molecular Medicine Today, vol. 6, Feb. 2000, pp. 72–81.*
Green et al. J. Am. Coll. Surg., vol. 191, No. 1, Jul. 2000, pp. 93–105.*
Aoki, K. et al., "Liposome–mediated in Vivo Gene Transfer of Antisense K–ras Construct Inhibits Pancreatic Tumor Dissemination in the Murine Peritoneal Cavity", *Cancer Research*, Sep. 1, 1995; 55:3810–3816.
Bertram, J. et al. "Reduction of erbB2 gene product in mamma carcinoma cell lines by erbB2 mRNA–specific and tyrosine kinase consensus phosphorothioate antisense oligonucleotides", *Biochem. Biophys. Res. Commun.*, Apr. 15, 1994; 200(1):661–667.
Bradley, M.O. et al. "Reversal of Transformed Phenotypes by Antisense fos", *Annals New York Academy of Sciences*, (1992); pp. 124–135.
Branch, A.D. "A good antisense molecule is hard to find", *TIBS*, Feb. 1998; 23:45–50.
Cheng, P.–W. "Receptor Ligand–Facilitated Gene Transfer: Enhancement of Liposome–Mediated Gene Transfer and Expression by Transferrin", *Human Gene Therapy*, Feb. 10, 1996; 7:275–282.
Crooke, S.T. "Basic Principles of Antisense Therapeutics", Chapter 1; Antisense Research and Application, ed. Stanley T. Crooke, Springer–Verlag, New York (Jul. 1998) pp. 1–50 plus 2 cover pages.
Daum, G. et al. "The ins and outs of Raf kinases", *TIBS*, Nov. 1994; 19:474–479.
Dean, N.M. et al. "Antisense oligonucleotides as inhibitors of signal transduction: development from research tools to therapeutic agents", *Biochem. Soc. Trans.*, 1996; 24:623–629.
Dzau, V.J. et al. "Fusigenic viral liposome for gene therapy in cardiovascular diseases", *Proc. Natl. Acad. Sci. USA*, Oct. 1996; 93:11421–11425.

(List continued on next page.)

*Primary Examiner*—Ram R. Shukla
*Assistant Examiner*—Jane Zara
(74) *Attorney, Agent, or Firm*—Rothwell, Figg, Ernst & Manbeck

(57) ABSTRACT

Provided are antisense oligonucleotides directed against the raf-1 gene, Ha-ras gene and HER-2 gene, components of a signal transduction pathway involving oncogenes and their normal counterparts and leading to the phenotype of cellular radioresistance. Administration of these antisense oligonucleotides is shown to reverse the radioresistance phenotype in cells overexpressing HER-2 or a mutant form of Ha-ras. Methods and compositions for reversing radiation resisting among other conditions involving these genes are disclosed.

32 Claims, 12 Drawing Sheets

OTHER PUBLICATIONS

Feero, W.G. et al. "Selection and use of ligands for receptor–mediated gene delivery to myogenic cells", *Gene Therapy*, 1997; 4:664–674.

Filion, M.C. et al. "Toxicity and immunomodulatory activity of liposomal vectors formulated with cationic lipids toward immune effector cells", *Biochimica et Biophysica Acta*, 1997;1329:345–356.

Flanagan, W.M. et al. "Cellular penetration and antisense activity by a phenoxazine–substituted heptanucleotide", *Nature Biotechnology*, Jan. 1999; 17:48–52.

Gewirtz, A.M. et al. "Facilitating oligonucleotide delivery; Helping antisense deliver on its promise", *Proc. Natl. Acad. Sci. USA*, Apr. 1996; 93:3161–3163.

Grimaldi, S. et al. "Attempts to use liposomes and RBC ghosts as vectors in drug and antisense therapy of virus infection", *Res. Virol.*, 1997; 148:177–180.

Gura, T. "Systems for Identifying New Drugs are Often Faulty", *Science*, Nov. 7, 1997; 278:1041–1042.

He, Y. et al. "Growth Inhibition of Human Papillomavirus 16 DNA–positive Mouse Tumor by Antisense RNA Transcribed from U6 Promoter", *Cancer Res.*, Sep. 15, 1997; 57:3993–3999.

Kasid, U. et al. "Effect of Antisense c–raf–1 on Tumorigenicity and Radiaton Sensitivity of a Human Squamous Carcinoma", *Science*, Mar. 10, 1989; 243:1354–1356.

Kasid, U. et al. "The raf Oncogene is Associated with a Radiation–Resistant Human Laryngeal Cancer", *Science*, Aug. 28, 1987; 237:1039–1041.

Kizaka–Kondoh, S. et al. "Raf–1 Protein Kinase is an Integral Component of the Oncogenic Signal Cascade Shared by Epidermal Growth Factor and Platelet–Derived Growth Factor", *Molecular and Cellular Biology*, Nov. 1992; 12(11):5078–5086.

Lappalainen, K. et al. "Cationic liposomes mediated delivery of antisense oligonucleotides targeted to HPV 16 E7 mRNA in CaSki cells", *Antiviral Research*, 1994; 23:119–130.

Lavigne, C. et al. "Enhanced Antisense Inhibition of Human Immunodeficiency Virus Type 1 in Cell Cultures by DLS Delivery System", *Biochem. Biophys. Res. Comm.*, 1997; 237:566–571.

Ledwith, B.J. et al. "Antisense–fos RNA Causes Partial Reversion of the Transformed Phenotypes Induced by the c–Ha–ras Oncogene", *Molecular and Cellular Biology*, Apr. 1990; 10(4):1545–1555.

Lee, R.J. et al. "Folate–targeted, Anionic Liposome–entrapped Polylysine–condensed DNA for Tumor Cell–specific Gene Transfer", *J. Biol. Chem.*, Apr. 5, 1996; 271(14):8481–8487.

Maher, L.J. et al. "Specific Hybridization Arrest of Dihydrofolate Reductase mRNA in Vitro Using Anti–sense RNA or Anti–sense Oligonucleotides", *Archives of Biochemistry and Biophysics*, Feb. 15, 1987; 253(1):214–220.

Morishita, R. et al. "Molecular Delivery System for Antisense Oligonucleotides: Enhanced Effectiveness of Antisense Oligonucleotides by HVJ–liposome Mediated Transfer", *J. Cardiovasc. Pharmacol. Therapeut.*, 1996; 2(3):213–222.

Plank, C. et al. "Activation of the Complement System by Synthetic DNA Complexes: A Potential Barrier for Intravenous Gene Delivery", *Human Gene Therapy*, Aug. 1, 1996; 7:1437–1446.

Renneisen, K. et al. "Inhibition of Expression of Human Immunodeficiency Virus–1 in Vitro by Antibody–targeted Liposomes Containing Antisense RNA to the env Region", *J. Biological Chemistry*, Sep. 25, 1990; 265(27):16337–16342.

Rojanasakul, Y. "Antisense oligonucleotide therapeutics: drug delivery and targeting", *Advanced Drug Delivery Reviews*, 1996; 18:115–131.

Ropert, C. et al. "Oligonucleotides Encapsulated in pH Sensitive Liposomes are Efficient Toward Friend Retrovirus", *Biochem. Biophys. Res. Commun.*, Mar. 16, 1992; 183(2):879–885.

Sepp–Lorenzino, L. et al. "Signal transduction pathways induced by heregulin in MDA–MB–453 breast cancer cells", *Oncogene*, 1996; 12:1679–1687.

Seth, P. et al. "Adenovirus–mediated Gene Transfer to Human Breast Tumor Cells: An Approach for Cancer Gene Therapy and Bone Marrow Purging", *Cancer Research*, Mar. 15, 1996; 56:1346–1351.

Simoes, S. et al. "Enhancement of Cationic Liposome–mediated Gene Delivery by Transferrin and Fusogenic Peptides", *Proceedings of the 24th International Symposium on Controlled Release of Bioactive Materials*, Jun. 15–19, 1997; 24:659–660.

Soldatenkov, V.A. et al. "Inhibition of Raf–1 Protein Kinase by Antisense Phosphorothioate Oligodeoxyribonucleotide is Associated with Sensitization of Human Laryngeal Squamous Carcinoma Cells to Gamma Radiation", *The Cancer Journal from Scientific American*, Jan./Feb. 1997; 3(1):13–20.

Stein, C.A. "Hybridization prediction gets to first base", *Nature Biotechnology*, Aug. 1999; 17:751–752.

Suy, S. et al. "Association of Grb2 with Sos and Ras with Raf–1 upon gamma irradiation of breast cancer cells", *Oncogene*, 1997; 15:53–61.

Tseng, B.Y. et al. "Antisense oligonucleotide technology in the development of cancer therapeutics", *Cancer Gene Therapy*, 1994; 1(1):65–70.

Vaughn, J.P. et al. "Inhibition of the erB–2 tyrosine kinase receptor in breast cancer cells by phosphoromonothioate and phosphorodhitioate antisense oligonucleotides", *Nucleic Acids Research*, 1996; 24(22):4558–4564.

Wagner, E. et al. "Influenza virus hemagglutinin HA–2 N–terminal fusogenic peptides augment gene transfer by transferrin–polylysine–DNA complexes: Toward a synthetic virus–like gene–transfer vehicle", *Proc. Natl. Acad. Sci. USA*, Sep. 1992; 89:7934–7938.

Wang, S. et al. "Delivery fo antisense oligodeoxyribonucleotides against the human epidermal growth factor receptor into cultured KB cells with liposomes conjugated to folate via polyethylene glycol", *Proc. Natl. Acad. Sci. USA*, 1995; 92:3318–3322.

Wang, Y. et al. "Prolonged Inhibition by X–Rays of DNA Synthesis in Cells Obtained by Transformation of Primary Rat Embryo Fibroblasts with Oncogenes H–ras and v–myc", Cancer Research, 1992; 52:508–514.

Xu, L. et al. "Transferrin–Liposome–Mediated p53 Sensitization of Squamous Cell Carcinoma of the Head and Neck to Radiation in Vitro", *Human Gene Therapy*, Mar. 1, 1997; 8:467–475.

Xu, M. et al. "Parenteral Gene Therapy with p53 Inhibits Human Breast Tumors In Vivo Through a Bystander Mechanism Without Evidence of Toxicity", *Human Gene Therapy*, Jan. 20, 1997; 8:177–185.

Zelphati, O. et al. "Synthesis and anti–HIV activity of thiocholesteryl–coupled phosphodiester antisense oligonucleotides incorporated into immunoliposomes", *Antiviral Research*, 1994; 25:13–25.

Zelphati, O. et al. "Antisense oligonucleotides in solution or encapsulated in immunoliposomes inhibit replication of HIV–1 by several different mechanisms", *Nucleic Acids Research*, 1994; 22(20):4307–4314.

* cited by examiner

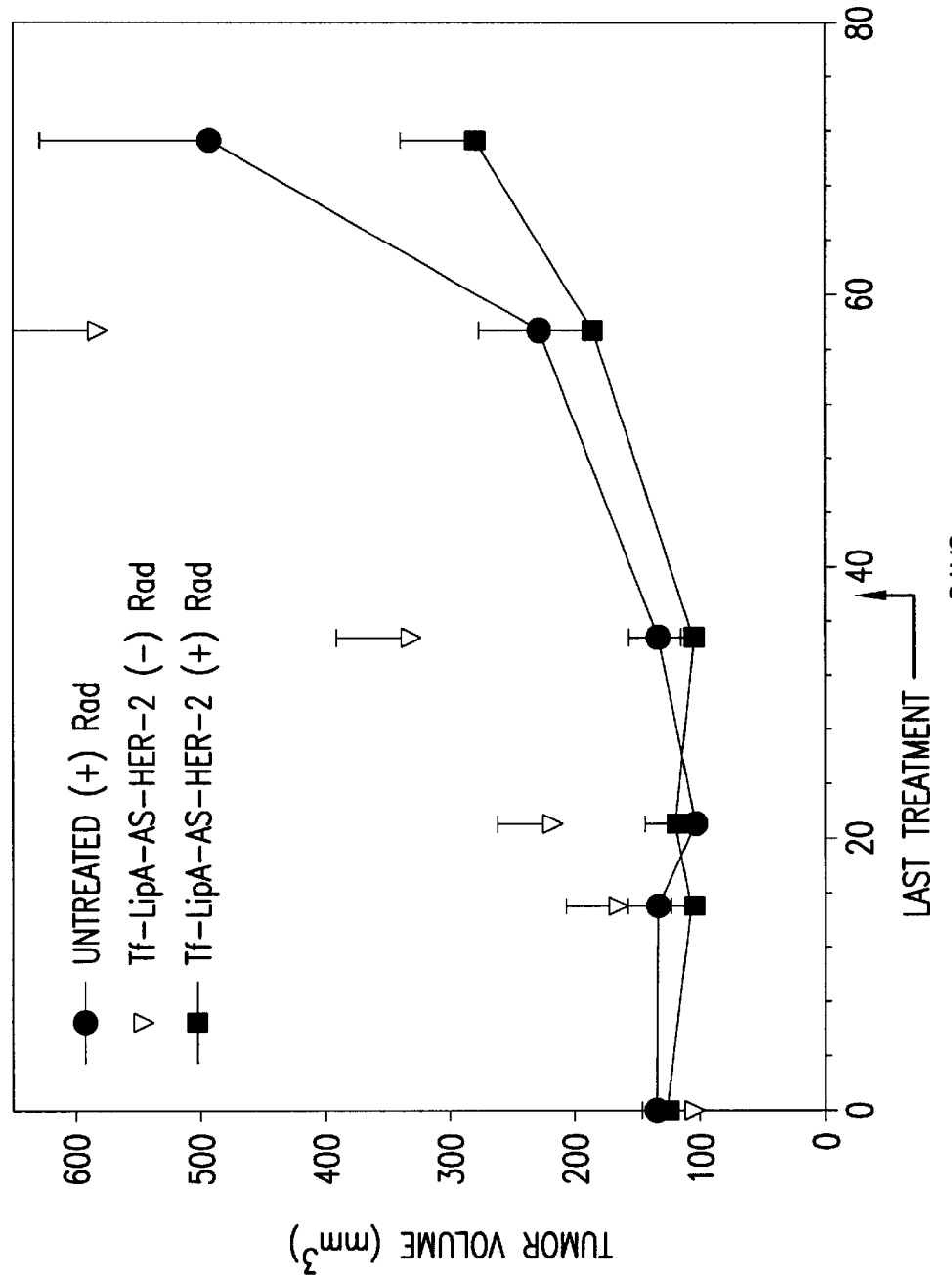

SEQUENCE LISTING

```
<160> NUMBER OF SEQ ID NOS: 9

<210> SEQ ID NO 1
<211> LENGTH: 18
<212> TYPE: DNA
<213> ORGANISM: Human

<400> SEQUENCE: 1
tccctgtatg tgctccat                                                 18

<210> SEQ ID NO 2
<211> LENGTH: 11
<212> TYPE: DNA
<213> ORGANISM: Human

<400> SEQUENCE: 2
tattccgtca t                                                        11

<210> SEQ ID NO 3
<211> LENGTH: 15
<212> TYPE: DNA
<213> ORGANISM: Human

<400> SEQUENCE: 3
tccatggtgc tcact                                                    15

<210> SEQ ID NO 4
<211> LENGTH: 18
<212> TYPE: DNA
<213> ORGANISM: Human

<400> SEQUENCE: 4
atggagcaca tacaggga                                                 18

<210> SEQ ID NO 5
<211> LENGTH: 18
<212> TYPE: DNA
<213> ORGANISM: Artificial Sequence
<220> FEATURE:
<223> OTHER INFORMATION: raf-1 control oligonucleotide scrambled

<400> SEQUENCE: 5
ctagcctatc tgtcttcg                                                 18

<210> SEQ ID NO 6
<211> LENGTH: 11
<212> TYPE: DNA
```

-continued

```
<213> ORGANISM: Artificial Sequence
<220> FEATURE:
<223> OTHER INFORMATION: Ha-ras control oligonucleotide scrambled 1

<400> SEQUENCE: 6
ttatacgtcc t                                                        11

<210> SEQ ID NO 7
<211> LENGTH: 11
<212> TYPE: DNA
<213> ORGANISM: Artificial Sequence
<220> FEATURE:
<223> OTHER INFORMATION: Ha-ras control oligonucleotide scrambled 2

<400> SEQUENCE: 7
ttatacgtcc t                                                        11

<210> SEQ ID NO 8
<211> LENGTH: 15
<212> TYPE: DNA
<213> ORGANISM: Artificial Sequence
<220> FEATURE:
<223> OTHER INFORMATION: HER-2 control sequence scrambled 1

<400> SEQUENCE: 8
cactggttgc acctt                                                    15

<210> SEQ ID NO 9
<211> LENGTH: 15
<212> TYPE: DNA
<213> ORGANISM: Artificial Sequence
<220> FEATURE:
<223> OTHER INFORMATION: HER-2 control oligonucleotide scrambled 2

<400> SEQUENCE: 9
ctagccatgc ttgtc                                                    15
```

COMPOSITIONS AND METHODS FOR REDUCING RADIATION AND DRUG RESISTANCE IN CELLS

CROSS-REFERENCE TO RELATED APPLICATIONS

This application is a continuation-in-part of application Ser. No. 09/480,143, filed Jan. 10, 2000, now abandoned, which is a continuation of application Ser. No. 08/991,830, filed Dec. 16, 1997, which issued on Feb. 22, 2000 as U.S. Pat. No. 6,027,892, which is related to provisional application Ser. No. 60/034,160, filed Dec. 30, 1996, and this application is also a continuation-in-part of application Ser. No. 09/601,444, filed Jan. 4, 2001, now U.S. Pat. No. 6,749,863, as PCT/US98/24657 and which is related to provisional application Ser. No. 60,/066,188, filed Nov. 19, 1997, and is also related to provisional application Ser. No. 60/083,175, filed Apr. 27, 1998, all of which are incorporated herein by reference in their entirety.

STATEMENT REGARDING FEDERALLY SPONSORED RESEARCH OR DEVELOPMENT

This invention was supported at least in part by a grant from the National Institutes of Health (HL48282). The United States government has certain rights in this invention.

BACKGROUND OF THE INVENTION

The failure of a significant number of tumors to respond to drug and/or radiation therapy is a serious problem in the treatment of cancer. While the genetic basis of this resistance in mammalian cells is still poorly understood, evidence has been obtained in recent years linking proto-oncogenes and oncogenes to the phenomenon of cellular radiation resistance.

The publications and other materials used herein to illuminate the background of the invention or provide additional details respecting the practice, are incorporated by reference, and for convenience are respectively grouped in the appended List of References.

The earliest report of such a possible link was that of FitzGerald et al. (1985), who found that transfection of NIH 3T3 cells with a human N-ras oncogene was able to increase the radiation resistance level of the recipient cell line. Expanding upon this was the report by Sklar (1988) that NIH 3T3 cells transformed not only by N-ras but also by mutated Ha- and Ki-ras were more radiation resistant than the parent cell line. Additionally, we demonstrated a similar effect on the radiation resistance level of NIH 3T3 cells by both the mutated form of Ha-ras and the overexpression of the Ha-ras proto-oncogene (Pirollo et al., 1989). A synergistic increase in the radiation resistance level of primary rat embryo cells was also seen after cotransfection of ras and myc oncogenes (Ling and Endlich, 1989; McKenna et al., 1990). All documents cited herein supra and infra are hereby incorporated in their entirety by reference thereto.

The association was extended to include other oncogenes when transfection of NIH 3T3 cells by high molecular weight DNA from both radiation-resistant cells derived from a human laryngeal squamous carcinoma (Kasid et al., 1987) and radiation-resistant noncancerous skin fibroblast (NSF) cell lines from members of a family with Li-Fraumeni syndrome (Pirollo et al., 1989; Chang et al., 1987) led to the identification of an activated human raf-1 oncogene in the resulting radiation-resistant transformants. Transfections not only of the raf-1 oncogene but also of other protein-serine kinase encoding oncogenes, mos and cot, have been shown to confer the radiation-resistant phenotype on the recipient human Beas-2B (Kasid et al., 1989), mouse NIH 3T3 (Pirollo et al., 1989), and hamster SHOK cells (Suzuki et al., 1992), respectively. The effect of activated oncogenes on the radiation resistance level of NIH 3T3 cells is not a generalized phenomenon but is particular to specific oncogenes, as was clearly shown by Sklar (Sklar, 1988; Sklar, 1986) for abl and fms and by our laboratory (Pirollo et al., 1989) for myc, fes, and abl.

Evidence continues to accumulate which indicates that the normal counterpart of many of the known oncogenes (proto-oncogenes) are involved in vital, normal cellular functions (Bishop, 1991; Cantley et al., 1991; Hunter, 1991). They have also been shown to interact with one another as components of a proposed signal transduction pathway which involves transmission of messages from the membrane to the nucleus directing the cells to divide or to differentiate. On the basis of antibody-blocking experiments, it has been proposed that raf-1 is downstream of ras in this pathway (Morrison, 1990; Rapp et al., 1988; Smith et al., 1986; Weinstein, 1988).

Part of the signal transduction pathway leading to raf-1 expression is HER-2 (c-erb B-2/neu) which encodes a transmembrane protein tyrosine kinase with extensive homology to the epidermal growth factor receptor (EGF-R). Elevation of HER-2 in cancer cells has been shown to correlate with failure to respond to radiation therapy and there is significant evidence that expression of HER-2 affects the response of breast cancer tumors to endocrine therapy with Tamoxifen, and chemotherapy using drugs such as cisplatin, carboplatin, 5-fluorouracil, mitoxantrone, cyclophosphamide, methotrexate, doxorubicin, carmustine, melphalan, mitomycin, etoposide and combinations of these drugs (Pegram et al., 1993; Wright et al., 1992; Allred et al., 1992; Gusterson et al., 1992; Van Diest et al., 1992; Muss et al., 1994; Tsai et al., 1993).

In addition to conventional adjuvant therapies, a new molecular therapy has shown promise in the treatment of breast cancer and is now in Phase III clinical trials. This new therapeutic, Herceptin (trastuzumab), is a humanized mouse antibody against the HER-2 receptor. HER-2 is a member of the epidermal growth factor family. Overexpression of HER-2 is associated with poor prognosis in breast cancer. The combination of Herceptin and chemotherapy has demonstrated increased response duration, time to progression and survival in clinical trials (Shak, 1999; Burris, 2000) and has been termed receptor-enhanced chemosensitivity. However, despite the promise of this new strategy, there are drawbacks. Overexpression of HER-2 is only found in approximately 25% of breast cancer patients, and it has been documented that Herceptin has no effect on cells that do not overexpress HER-2 (Pegram and Slamon, 1999), the majority of breast cancers. Moreover, some HER-2 positive tumors have not responded to Herceptin (McNeil, 2000). Most significant is the increase in cardiac toxicity observed when patients received the combination of Herceptin and either doxorubicin or cyclophosphamide, two drugs routinely used in the treatment of breast cancer (McNeil, 2000; Jerian and Keegan, 1999; Gilewski et al, 2000; Schaller, 1999).

Recent studies indicate that the radiation resistant (RR) phenotype appears to be linked to the activation of specific protooncogenes in a signal transduction pathway involving HER-2 as an upstream member of the pathway and Ha-ras and raf-1 downstream of HER-2, analogous to that described for cell growth and differentiation (Pirollo et al., 1993). We hypothesized that disruption of the pathway therefore should lead to reversal of this phenotype and increased sensitivity of resistant cells to drug/radiation therapy which would have far-reaching clinical implications in the treatment of drug and radiation resistant tumors.

SUMMARY OF THE INVENTION

A specific strategy to interfere with the signaling is to modulate the expression of specific genes in the pathway at the RNA level using antisense oligonucleotides (ASO). Short antisense DNA oligonucleotides selectively bind to cellular mRNA targets through complementary sequence-specific Watson-Crick base pairing. The hydrogen-bonded antisense molecule can modulate the expression of the targeted gene product (Uhlmann and Peyman, 1990). We and others have demonstrated the ability of antisense oligonucleotides and their modified analogues to specifically inhibit ras p21 protein synthesis in in vitro translation, in cell culture, and in tumorigenesis in nude mice (Yu et al., 1989; Brown et al., 1989; Chang et al., 1991; Ts'o et al., 1992; Plenat, 1996). Additionally, ASO against genes such as c-myb, c-myc, c-fos, BCR-ABL and the IGF receptor, have also been shown to suppress human tumor cell growth in vitro and in some cases are currently in clinical trials as anti-cancer therapeutics (Stein et al., 1988; Mercola and Cohen, 1995; Scanlon et al., 1995).

The serine/threonine kinase Raf-1 protein appears to be a central component of multiple signal transduction pathways in the cell (reviewed in Campbell et al., 1995; Daum et al., 1994) including that for radiation resistance. Consequently, the use of ASO against raf-1 itself, or against upstream effectors of raf-1 such as Ha-ras and HER-2, to impede signaling through this gene should result in increased drug and radiation sensitivity, which would have-far-reaching clinical implications in the treatment of radioresistant tumors.

Therefore, the present invention relates to a method for reversing the drug and radiation resistance phenotype of cells, more specifically tumor cells which have acquired drug and/or radiation resistance. The method of the present invention employs antisense oligonucleotides targeted against specific proto-oncogenes in the signal transduction pathway leading to the radiation resistant phenotype. More specifically, the method employs the administration of antisense oligonucleotides complementary to unique sequences of HER-2 genes such that the expression of this factor is reduced, and the cells are radiosensitized.

Therefore, it is an object of the present invention to provide antisense oligonucleotides for reverting radiation and drug resistant cells in vitro and in vivo, for use in diagnostic assays for detecting expression of genes in the signal transduction pathway leading to radiation and/or drug resistance, and for use as therapeutic agents for inhibiting tumor cell growth to improve response to conventional therapeutics and therefore improve survival.

It is another object of the present invention to provide a method for decreasing raf1, Ha-ras, or HER-2 expression important in reverting radiation resistant cells to radiation sensitive cells or to reduce symptoms of diseases resulting from the overexpression of these genes. For example, it is possible to inhibit restenosis, abnormal wound repair, or any biological activity which is produced by signaling through these pathways. These genes are involved in multiple signal transduction pathways, one of which, the MAPK pathway, is considered antagonistic to apoptosis. Perturbation of the signal transduction pathways by these antisense oligonucleotides may lead to or potentiate apoptosis. Ras signaling through the Ras/MAPK pathway may also play a role in formation of long-term memory and abnormal expression may therefore impact on disease states such as senility and Alzheimer's. Mutated Ras acting through a different signaling pathway, inhibits skeletal muscle differentiation. A mutation in a member of the raf family, A-raf, was found in mice to lead to neurological and gastrointestinal abnormalities and death in mice. Elevated levels of a fragment of HER-2 protein found in sera was considered a possible cause of pre-eclampsia or HELLP syndrome in pregnant women. Therefore, decreasing expression of these genes may be important in reversing or reducing these conditions and diseases.

It is a further object of the present invention to provide a method to resensitize radiation- and drug-resistant cells, the method comprising administering to the cells antisense oligonucleotides of genes identified in the signal transduction pathway leading to resistance such as oligonucleotides of the present invention. Other genes involved in the MAPK signal transduction pathway are defined in FIG. 6. Applicants have found that growth factor sis (PDGF-$\beta$), receptor tyrosine kinases trk (nerve growth factor), met (hepatocyte growth factor), tyrosine kinase src, serine/threonine kinase mos, protein kinase C $\beta$-1, nuclear oncogene ets-1, as well as some other components of the MAPK pathway, are involved in the radiation resistant phenotype, and administration of oligonucleotides which block the transduction pathway through these and other genes in this pathway may reduce the radiation resistance phenotype (Pirollo et al., 1993). This method is important in the treatment of tumors, especially tumors which have acquired resistance to radiation and drugs, both endocrine and chemical.

It is yet another object of the present invention to provide a method for inhibiting tumor growth by reducing levels of raf-1, Ha-ras or HER-2 in said tumor, thereby resensitizing radiation- and drug-resistant cells in the tumor to radiation and drugs such that these cells can be treated again with either radiation or drugs.

It is still another object of the present invention to provide a method for detecting the level of raf-1, Ha-ras or HER-2 RNA in a cell comprising labeling the antisense oligonucleotides of the present invention and using the labeled oligonucleotides in a hybridization assay or a polymerase chain reaction (PCR) assay to detect the presence of the gene or amount of raf-1, Ha-ras and HER-2 RNA in a cell.

It is yet another object of the present invention to provide a therapeutic agent for treating diseases associated with an increase in raf-1, Ha-ras and HER-2, such as cancer, for example, the agent comprising the antisense oligonucleotides of the present invention in a pharmaceutically acceptable amount, in a pharmaceutically acceptable excipient.

It is further another object of the present invention to provide a method for visualizing raf-1, Ha-ras and HER-2 RNA in an organism, said method comprising labeling the antisense oligonucleotides of the present invention with a detectable label useful for imaging, and administering the labeled oligonucleotides at the site where imaging is desired, and detecting the label.

BRIEF DESCRIPTION OF THE DRAWINGS

These and other features, aspects, and advantages of the present invention will become better understood with reference to the following description and appended claims, and accompanying drawings where:

FIG. 1A—Western blot analysis of Raf-1 protein synthesis inhibition by increasing concentrations of raf-1 oligonucleotides. C=untreated cells; 0=cells treated with liposomes but no oligonucleotides; AS=antisense; S=sense. FIG. 1B—Histogram demonstrating radiosensitization with increasing concentrations (0.1, 0.3, 1 $\mu$M) of anti-raf-1 ASO. As controls, the cells were treated with 1 $\mu$M of either a sense or a scrambled raf-1 oligonucleotide. Radioresistance levels are given as $D_{10}$ values. Error bars represent the standard error of the mean (S.E.M.) of 2 to 13 values.

FIG. 3A—JSQ-3 and FIG. 3B—SK-OV-3 cells untreated or treated with either 1 $\mu$M raf-1 antisense or sense oligonucleotides. Curves are plotted as the log of the surviving fraction vs. radiation dose in Gy. Points are plotted as the S.E.M. of 2–13 values.

FIG. 5A—Western blot analysis of HER-2 protein synthesis inhibition by increasing concentrations (0.3, 1.0 and 3.0 $\mu$M) of HER-2 oligonucleotides. C=untreated cells; 0=cells treated with liposomes but no oligonucleotides; AS=antisense; S=scrambled. FIG. 5B—Histogram demonstrating radiosensitization by HER-2 ASO. The concentration of antisense HER-2 oligonucleotide used to treat T24 and MCF10A was 1 $\mu$M. As controls, the cells were treated with 1 $\mu$M of two different scrambled HER-2 oligonucleotides. Radioresistance levels are given as $D_{10}$ values. Error bars represent the S.E.M. of 2–7 values.

FIG. 11. Graph showing time course of tumor volume in mice treated with radiation, Tf-LipA-AS-HER-2, and radiation plus Tf-LipA-AS-HER-2.

DETAILED DESCRIPTION OF THE INVENTION

Figure 1A:
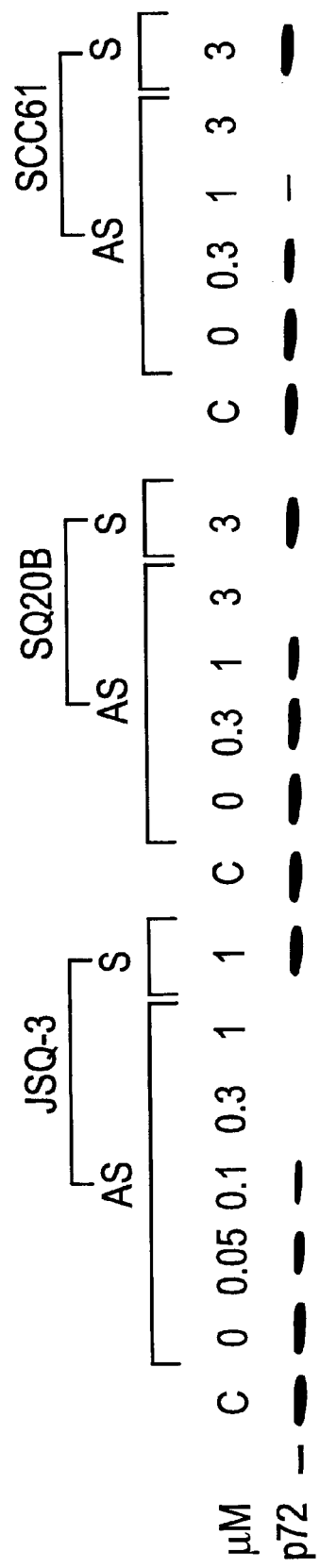
FIGS. 1A–B. The effect of anti-raf-1 oligonucleotides on Raf-1 p72 protein synthesis and the radiation resistance levels of SCCHN cell lines JSQ-3 and SQ-20B.

As was discussed above, previous studies have indicated the presence of a signal transduction pathway, leading to cellular radiation resistance. We hypothesized that inhibiting or reducing the expression of members of this pathway in cells should block signaling leading to decreased radioresistance. Members of this pathway include, but are not limited to, raf-1, Ha-ras and HER-2. One method for reducing the expression of these genes is through antisense oligonucleotides or ribozymes.

Therefore, in one embodiment, the present invention relates to a composition of matter consisting essentially of at least one antisense oligonucleotide substantially complementary to an RNA sequence (mRNA or pregenomic RNA) encoded by the HER-2 gene, preferably at or near the initiation codon of HER-2, at about nucleotides 708 to 718, or around the promoter sequence or at single stranded loops based on secondary structure. The oligonucleotide is preferably comprising a sequence of at least about 8 nucleotides, is preferably not more than about 40 nucleotides, more preferably about 15–20 nucleotides, and optimally about 11 nucleotides.

As used herein, "substantially complementary" means that an antisense oligonucleotide of the invention is capable of hybridizing with its RNA target under physiological conditions, e.g., as pertains inside a cell expressing HER-2. Whether or not a sequence is substantially complementary can be determined by techniques known to those with ordinary skill in the art. For example, the sequence of the antisense oligonucleotide can be compared to the HER-2 sequence (Coussens, 1985) and its ability to hybridize to RNA under appropriate stringency conditions can be determined. Hybridization techniques are known in the art. See for example, Ausubel et al. (1992).

As used herein, "consisting essentially of" has its usual meaning, i.e., that one or more compositions of matter of the invention may be used together, either in admixture or combined in a single molecule, with other materials that do not alter the essential nature of the invention. For example, while the antisense oligonucleotide sequences of the invention are essential to the invention, it is contemplated that they may be used in admixture or in chemical combination with one or more other materials, including other oligonucleotides, materials that increase the biological stability of the oligonucleotides, or materials that increase their ability to selectively penetrate their target cells and reach and hybridize to their target RNA. Furthermore, the term "oligonucleotide" includes derivatives thereof, such as backbone modifications, e.g., phosphorothioate derivatives, employed to stabilize the oligonucleotide. All such modifications are contemplated equivalents of the antisense oligonucleotides of the invention. The following discussion provides examples of the kinds of modifications that may be employed, but those of skill in the art will readily recognize others. Non-naturally occurring backbones carrying bases and capable of base pairing to natural nucleic acids both known and not as yet invented, may be substituted for DNA or RNA oligonucleotides; such backbones may prove more stable than DNA or RNA. For example, the antisense oligonucleotides may be provided in stabilized form, e.g. with phosphotriester linkages, or by blocking against exonuclease attack with methylphosphonodiester linkages, with 3' deoxythymidine, as a phenylisourea derivative, or by linking other molecules such as aminoacridine or polylysine to the 3' end of the oligonucleotide. See, e.g., Tidd (1990), the teaching of which is incorporated herein by reference. Though exemplified herein by single-stranded DNA molecules, it will be recognized that non-DNA backbones may be substituted. For instance, an RNA or RNA-DNA hetero-oligomer antisense molecule would be useful if one desired the antisense sequence to be less stable or more tightly binding than a DNA oligonucleotide. Base analogues may be substituted for the commonly found A (adenosine or deoxyadenosine), G (guanosine or deoxyguanosine), C (cytidine or deoxycvtidine), T (thymine) or U (uridine). Examples include, but are not limited to, 7-aza-G and 5-methyl-C. Such base analogues are useful for adjusting Tm of an oligonucleotide or a segment thereof. Tm, or melting temperature, is a measure of binding between two strands of a double-stranded nucleic acid. Substitution of rT (ribothymidine) for U or dU (deoxyuridine) for T are also possible. Other strategies include attaching oligonucleotides to DNA-protein complexes or cationic liposomes as exemplified in the Examples following.

For antisense oligonucleotides supplied exogenously, preferably as part of a liposome complex, increased selectivity for cell type may be achieved by linking the antisense oligonucleotide-liposome complexes of the invention to natural ligands of the target cell or cell-specific antibodies, or to synthetic ligands that will bind to the target cell. The oligonucleotide may also be at least partially double stranded, either by binding to a distinct oligonucleotide or by formation of a hairpin, either at one or both termini or internally as long as the oligonucleotide is still able to decrease expression of the desired gene in a cell.

The present invention is not limited to any particular method of making the antisense oligonucleotides. The antisense oligonucleotides may be produced by any method known to the art. While those exemplified herein were synthesized using an automated synthesizer, expressed nucleotides made by an expression vector used for gene therapy, such as an adenoviral, retroviral, or plasmid vector can be designed to produce antisense RNA when introduced into a cell. Use of other synthetic chemistries is possible, see for example, Uhlmann and Peyman (1990). Other methods of making these oligonucleotides will be evident to those with skill in the art. It will be recognized by those in the art that having shown that the invention is operative with the exemplified oligonucleotides and in accordance with other teachings of the present invention, those of ordinary skill in the art are enabled to design and test oligonucleotides not exemplified herein, that arc also operative.

In another embodiment, the present invention relates to compounds for use in the treatment or diagnosis of disease. The compounds of the present invention are antisense oligonucleotides as described above, able to reduce the expression of the gene they target, specifically, HER-2, as well as reducing the expression of other genes in the pathway utilizing HER-2 or related pathways, e.g., use of HER-2 antisense oligonucleotides to decrease the expression of raf-1 or Ha-ras. The compounds of the present invention can be used as therapeutic agents to treat or diagnose disorders or diseases related to the expression of raf-1, Ha-ras or HER-2. Such diseases include but are not limited to, cancer, restenosis, osteoarthritis, neurological and intestinal abnormalities, pre-eclampsia, among others.

The compounds of the present invention may be used to detect the level or presence of raf-1, Ha-ras or HER-2 RNA or DNA in a sample, said sample being a cell, cell extract, purified DNA or RNA from cells, tissue, or organ, or sections of tissues or organs, or diagnose an increase in raf-1, Ha-ras or HER-2 RNA in a cell, by detecting raf-1, Ha-ras or HER-2 RNA. The level of raf-1, Ha-ras or HER-2 RNA can be detected by extracting cellular RNA and detecting the level of raf-1, Ha-ras or HER-2 RNA using a hybridization assay, such as a Northern hybridization assay wherein the antisense oligonucleotides are labeled with a detectable label, or alternatively, by in situ assay of a cell or organ or tissue section using in situ hybridization techniques known to persons of skill in the art. In addition, the compounds of the present invention can be used in a polymerase chain reaction assay as primers for the detection of raf-1, Ha-ras or HER-2 RNA or DNA in cells by methods well known in the art. The compounds of the present invention may be labeled using any of a variety of labels and methods of labeling. Examples of types of labels which can be used in the present invention include, but are not limited to, enzyme labels, radioisotopic labels, non-radioactive isotopic labels, fluorescent labels, and chemiluminescent labels. Such assays may also be useful for in vitro testing of potential drugs for treating a disease involving raf-1, Ha-ras or HER-2 RNA, such as cancer, or to monitor the effect of the drug on raf-1, Ha-ras or HER-2 RNA expression. Cell lines useful for in vitro drug testing would be those expressing raf-1, Ha-ras or HER-2 RNA. For instance, cells expressing Ras include, but are not limited to, T24, Hs578T, SK-CO-1, Calul among others (Bos, 1998). Cells expressing Raf-1 include, but are not limited to, SQ-20B, JSQ-3 and other SCCHN cell lines, among others (Weichselbaum et al., 1988; Weichselbaum et al., 1986). Cells expressing HER-2 include, but are not limited to SK-OV-3, ZR-75-1, MDA-MB435, and NDA-MB-453, among others.

As was discussed above, a signal transduction pathway, with raf-1, Ha-ras or HER-2 as central elements, leads to cellular drug resistance and radioresistance. Chemotherapy and radiation are two major forms of adjuvant therapy for various types of cancer. The ability to revert drug/radiation resistant tumor cells thereby rendering them drug/radio-sensitive and vulnerable to drug and radiation treatments, provides a valuable method in the treatment of tumors. The antisense oligonucleotide compositions of the present invention are able to ameliorate or revert the drug resistance and radioresistance of tumor cells. Raf-1 expressing tumors include stomach, and squamous cell carcinoma of the head and neck (upper aero-digestive track); ras expressing tumors include bladder, breast, lung, colon, pancreas, prostate; HER-2 expressing tumors include breast, ovarian, cervical, lung, prostate, head and neck cancers.

The oligonucleotides can be used in a method for treating diseases or conditions involving raf-1, Ha-ras or HER-2 expression, or where the modulation of these genes is desired. The method would include administering an effective amount of one or more of the compounds of the present invention, or one or more HER-2 antisense oligonucleotide (s) to a patient requiring such a treatment, such that the level of the targeted RNA or protein is decreased. The antisense oligonucleotides can be prepared for administration by methods known in the art which can include filtering to sterilize the solution of antisense oligonucleotides, diluting or concentrating the solution, adding a stabilizer to the solution, lyophilizing the solution to produce the oligonucleotides in dried form for ease in transportation and storage. Improvement of oligonucleotide uptake has been achieved with different systems of vectorization including liposomes (neutral, cationic, inmunoliposome), nanoparticles, or covalent attachment of a carrier. Advantageously, the antisense oligonucleotides are combined with "sterically stabilized" liposomes (S-liposomes) which have been developed and are suitable for therapeutic applications such as sustained drug release and selective delivery of drugs to specific targets (reviewed in Allen (1994) and Gregoriadis and Florence (1993)). Long circulating half-lives and the ability of the S-liposomes to localize in high concentration in solid tumors make them useful in cancer treatment. The liposome-antisense delivery can be passive for example by simple fusion with the cell, or active by attachment of antibodies or other proteins to the liposome surface to cause specific targeting (Allen, 1994; Mori et al., 1991), for example, use of transferrin or folate as a targeting ligand. Further, the antisense oligonucleotide treatment solution can be in the form of a mixed solution which contains the antisense oligonucleotides described above and at least one other antigen or oligonucleotide, as long as the added compound does not interfere with the effectiveness of the antisense oligonucleotide treatment and adverse reactions such as toxicity are not increased additively or synergistically.

The present invention uses systemic or intratumoral administration of a ligand/cationic liposomal delivery complex for tumor-targeted delivery of a therapeutic molecule via receptor-mediated endocytosis. The therapeutic molecule is targeted and effectively delivered to tumor cells. In a preferred embodiment, the therapeutic molecules being delivered are antisense oligonucleotides directed against genes in the cell growth pathway. Down-modulation of these genes results in sensitization of the tumor cells and xenografts to radiation and chemotherapeutic agents.

The present invention provides a new and improved method for accomplishing cancer gene therapy by providing a systemic delivery system ("complex") that specifically targets tumor cells, including metastases, and results in a more effective cancer treatment modality. This method uses a ligand-directed cationic liposome system to deliver a therapeutic molecule to the tumor cells. The inclusion of a cell-targeting ligand (e.g. the folate or transferrin ligand) in the liposome-DNA complex takes advantage of the tumor-targeting facet and receptor-mediated endocytosis associated with the ligand to introduce a therapeutic molecule efficiently and specifically to the tumor cells in vivo as well as in vitro.

The invention of this application is superior to the therapeutic modality described above (Herceptin) in that it has a much broader application in the treatment of breast cancer. It covers both unelevated, low expressed and highly expressed tumors. Since overexpression of the HER-2 gene is not a prerequisite, the use of the ligand-directed liposome delivered AS-HER-2 oligodeoxynucleotide is not limited to only a small percent of the patient population. The inability to identify a ligand specific for HER-2 has led to the hypothesis that it functions, at least in part, as a co-receptor with the other members of the ErbB family of growth factor receptors (Klapper et al., 2000). The four ErbB family members, ErbB-1, ErbB-2/HER-2, ErbB-3 and ErbB-4 form homo- and heterodimer complexes upon ligand binding thus inducing their kinase activity and producing intracellular signals activating cell growth control pathways such as MAP-kinase. HER-2 has been proposed to be the preferential dimer-mate for each of the other three family members (Tzahar and Yarden, 1998; Klapper et al., 2000). This results in a signaling network that can respond to a myriad of ligands and interact with a large number of effector proteins.

More significantly, this heterodimerization between HER-2 and other family members may explain the ability of AS-HER-2 ODN's (oligodeoxynucleotides) to be effective in tumor cells that have an apparently normal level of HER-2. These and other tumor cell lines may possess abnormalities in other ErbB family members resulting in aberrant cell growth signaling. Because of the preference for HER-2 within the heterodimer complexes, it is conceivable that down-modulation of HER-2 via AS ODN would effect signaling through heterodimers where it is the HER-2 partner, not HER-2 itself, that is abnormal. Moreover, there is a high level of crosstalk between the innumerable signal transduction pathways which exist within the cell. Down modulation of HER-2, even if not overexpressed, which is at the head of some of these pathways may, through this crosstalk, also indirectly influence signaling through other pathways in which it is not directly involved.

The apparent broad range of effectiveness of AS-HER-2 ODN indicates that this technology could be a viable clinical treatment modality for breast cancer. Furthermore, the lowering of the effective dose of conventional chemotherapeutic agents, with a concomitant decrease in their toxic side-effects, would be of substantial benefit to breast cancer patients. In particular, sensitization of breast tumors to doxorubicin would decrease the cardiac toxicity associated with the use of this chemotherapeutic agent.

There are numerous reports of attempts to use cationic liposomes as delivery vehicles for AS ODN's (Semple et al., 2000). These include delivery of antisense c-myb (Pagnan et al., 2000), c-raf (Gokhale et al., 1997) which has just entered clinical trials, β-endorphin (Fresta et al., 1998), the Leshmania universal miniexon sequence (Chakraborty et al., 1999) and HER-2 (Meyer et al., 1998). These studies indicate that the use of cationic liposomes as a carrier for antisense molecules results in increased stability, intracellular uptake and biological activity. However, while some attempts have been made to use monoclonal antibodies to target the complex to tumor cells in vitro (Pagnan et al., 2000), none of these approaches uses ligands (folate or transferrin) to target the liposome-antisense complex preferentially to tumors. Our approach is superior in that using folate or transferrin as the targeting ligand should also result in a smaller complex than one containing a monoclonal antibody. Thus, this smaller size would permit superior tumor penetrance. Moreover, with our complex we have been able to treat preexisting tumors with abnormalities in genes other than HER-2 with a low concentration of antisense HER-2 (approximately 0.6 $\mu$M in the test animals) resulting in increased radiation sensitivity and significant inhibition of tumor growth. Our ligand-liposome-antisense HER-2 complex also demonstrated superior transfection efficiency as demonstrated by the extremely low efficacious antisense concentration. Additionally, systemic delivery of AS-HER-2 via the ligand-liposome complex resulted in superior tumor uptake and retention as compared to the uncomplexed antisense molecule.

Thus, this ligand-directed, tumor targeting liposome delivery system for antisense HER-2 can be applied to a broad spectrum of tumors and is not limited only to breast cancers.

The exemplified liposome compositions are based upon the cationic lipid dioleoyltrimethylammonium-propane (DOTAP) and fusogenic neutral lipid dioleoylphosphatidylethanolamine (DOPE) conjugated (e.g. esterified) to either folic acid (to provide a folate ligand thereon) or simply mixed with iron-saturated transferrin. The ratio of lipids themselves, as well as the lipid:DNA ratio, will be optimized for in vivo delivery, as well as for different tumor cell types, e.g. adenocarcinoma vs. squamous cell carcinoma. In vitro studies demonstrated that the addition of the ligand substantially increased the transfection efficiency for tumor cells when compared to the liposome alone, even in the presence of high levels of serum.

The in vivo tumor targeting capability of this system was assessed using the β-galactosidase reporter gene in three different types of cancer—SCCHN, breast cancer and prostate cancer. These studies demonstrated that after intravenous administration of the complexes, only the tumors were transfected, with an efficiency between 50 and 70%, while normal organs and tissues, including the highly proliferative bone marrow and intestinal crypt cells, showed no signs of reporter gene expression. Some ligand-liposome-DNA complex was evident in macrophages. Very significantly, even micrometastases in the lung, spleen and lymph nodes showed evidence of highly efficient and specific transfection.

When the systemically delivered ligand-liposome wtp53 complex was administered to mice bearing radiation resistant human SCCHN xenografts, and followed with radiation therapy, the tumors completely regressed. Histological examination of the area of the former tumor showed only normal and scar tissue remaining, with no evidence of live tumor cells. This was in contrast to the tumors from animals treated only with the ligand-liposome-p53 complex or only with radiation. In these animals some cell death was evident. However, nests of live tumor cells remained, resulting in the regrowth of the tumors in these animals. Strikingly, no recurrence of the tumors was evident in the animals receiving the combination therapy, even one year after the end of treatment. Similar results were observed in mice bearing human prostate tumor xenografts with radiation and chemotherapeutic agents, as well as with human breast cancer and pancreatic cancer xenografts with chemotherapeutic agents. Consequently, this system is viewed as providing a more effective form of cancer therapy.

The uptake of the ligand-liposome-therapeutic molecule complex by the target cells will, when administered in conjunction with adjuvant therapies, and when the target cells are cancer cells, not only decrease the rate of proliferation of these cells but actually result in increased tumor cell death and long-term tumor regression. The delivery system of the invention strongly portends a prolongation of patient survival.

Even though the invention has been described with a certain degree of particularity, it is evident that many alternatives, modifications, and variations will be apparent to those skilled in the art in light of the present disclosure. Accordingly, it is intended that all such alternatives, modifications, and variations which fall within the spirit and the scope of the invention be embraced by the defined claims.

The antisense oligonucleotide treatment solution may be stored in a sealed vial, ampule or the like. The present treatment can be administered in the form of a spray for intranasal administration, or by nosedrops, inhalants, eye drops, skin patch, suppository, mini-pump implant, or a capsule, liquid suspension or elixirs formulated for oral administration. In the case where the treatment is in dried form, the treatment can be dissolved or suspended in sterilized distilled water or saline before administration. Any inert carrier is preferably used, such as saline, phosphate buffered saline, or any such carrier in which the antisense oligonucleotides have suitable solubility.

Generally, the method of administration or treatment may depend on the organ or organs targeted. The compounds or treatment may be administered orally, subcutaneously, intratumorally, intravenously, or intramuscularly or intracranially by direct injection. For example, in the lung, the composition would be administered as an inhalant, or intravenously; in the breast, head or neck, intravenously or direct injection; in the bladder, ovaries, or pancreas, intravenously. These methods of administration are known to persons of skill in the art.

The compounds of the present invention can be administered in a dose effective for the production of a decrease in raf-1, Ha-ras or HER-2 and resulting in an improvement of the patient's disease, or amelioration of the patient's disease symptoms. The treatment may be in the form of a single dose or in a multi-dose program. At low (sub-optimal) concentrations of the oligonucleotides, the effect maybe additive or even synergistic. When providing a patient with antisense oligonucleotides, the dosage administered will vary depending upon such factors as the patient's age, weight, height, sex, general medical condition, previous medical history, etc. In general, it is desirable to provide the recipient with a dosage of the above compounds which is in the range of 1 pg/kg to 500 mg/kg (body weight of patient), although a lower or higher dosage may be administered.

Described below are examples of the present invention which are provided only for illustrative purposes, and not to limit the scope of the present invention. Other suitable modifications and adaptations of the variety of conditions and parameters normally encountered in this art which are obvious to those skilled in the art are within the spirit and scope of the present invention.

The following MATERIALS AND METHODS were used in the examples that follow.

Oligonucleotides

Phosphorothioated ASO directed at or near the initiation codon were synthesized by Midland Certified Reagent Co., Midland, Tex. for the raf-1 (5'-TCCCTGTATGTGCTCCAT-3') (SEQ ID NO:1), Ha-ras (5'-TATTCCGTCAT-3') (SEQ ID NO:2), and HER-2 (5'-TCCATGGTGCTCACT-3') (SEQ ID NO:3) genes.

Two controls for each gene, either a sense and a scrambled (for raf-1) or two different scrambled (for Ha-ras and HER-2) oligonucleotides were also synthesized. The scrambled oligomers have the same base composition as antisense but in a different, random order. The sequences for the raf-1 controls are 5'-ATGGAGCACATACAGGGA-3' (sense) (SEQ ID NO:4) and 5'-CTAGCCTATCTGTCTTCG-3' (scrambled) (SEQ ID NO: 5); for Ha-ras 5'-TTATACGTCCT-3' (scrambled 1) (SEQ ID NO:6) and 5'-TTATACGTCCT-3' (scrambled 2) (SEQ ID NO:7); and for HER-2 5'-CACTGGTTGCACCTT-3' (scrambled 1) (SEQ ID NO:8) and 5'-CTAGCCATGCTTGTC-3' (scrambled 2) (SEQ ID NO:9).

Cell Culture and Treatment

Squamous cell carcinoma of the head and neck (SCCHN) cell lines JSQ-3 (Weichselbaum et al., 1988), SQ-20B (Weichselbaum et al., 1986) and SCC-61 (Weichselbaum et al., 1986), which were kind gifts from Dr. Ralph Weichselbaum. University of Chicago, were maintained in Minimum Essential Medium with Earle's salts (EMEM), supplemented with 10% heat inactivated fetal bovine serum; 50 µg/ml each of penicillin, streptomycin and neomycin; 2 mM L-glutamine; 0.1 mM non-essential amino acids, 1 mM pyruvate and 0.4 µg/ml hydrocortisone. Human ovarian (SK-OV-3) and bladder (T24) carcinoma cell lines (obtained from ATCC, Rockville, Md.) were maintained in McCoy's 5A medium supplemented with 10% fetal bovine serum, 50 µg/ml each of penicillin, streptomycin and neomycin and 2 mM L-glutamine. Normal human non-tumor breast cell line MCF 10A (ATCC, Rockville, Md.) was maintained in a 1:1 mixture of Dulbecco's modified Eagle's medium and Ham's F12 medium supplemented with 5% horse serum, 20 ng/ml epithelial growth factor, 100 ng/ml cholera toxin, 0.01 mg/ml insulin, 500 ng/ml hydrocortisone, 50 µg/ml each of penicillin, streptomycin and neomycin and 2 mM-glutamine.

For oligonucleotide treatment, the cells were plated at 1×10$^5$ cells/well in 6-well tissue culture plates. Twenty-four hours later, at approximately 40–60% confluency, the cells were transfected with the oligonucleotides, facilitated by Lipofectin Reagent, using essentially the protocol supplied by the manufacturer, Life Technologies, Inc. After 6 hours, the lipofection solution was removed and the monolayer washed with fresh medium containing 8 mM L-glutamine and 20% serum. The cells were then incubated for an additional 16–18 hours in 1 ml of this medium.

Radiobiology

Cellular response to radiation was evaluated by the colony survival assay. Exponentially growing monolayer cultures of each cell line were treated with the oligonucleotides as described above. The cells were harvested 24–48 hours later, suspended in fresh medium and irradiated at room temperature with graded doses of $^{137}$Cs γ rays at a dose of approximately 36 Gy/minute in a J. L. Shepard and Associates Mark Irradiator. Afterward, the cells were diluted and plated at a concentration of 300 to 5000 cells per well in a 6-well tissue culture plate. Two to three days after plating, the cells were supplemented with 0.5 ml of serum plus 5 µg/ml hydrocortisone. Approximately 7–14 days later, the cells were stained with 1% crystal violet and colonies (comprising 50 or more cells of normal appearance) were scored. Survival curves were plotted as the log of the survival fraction versus the radiation dose using Sigma-Plot Graphics program. $D_{10}$ (the dose required to reduce survival to 10%) values were calculated from the initial survival data.

Protein Analysis

After oligonucleotide treatment, cells for protein analysis were trypsinized, pelleted, rinsed with PBS and lysed in RIPA buffer (1% NP40, 0.5% sodium deoxycholate, 0.1% SDS, 30 µg/ml aprotinin and 1 mM sodium orthovanidate in PBS) (Santa Cruz Biotechnology, Inc). After shearing with a 26 gauge needle, 100 µg/ml Phenylmethylsulfonyl fluoride (PMSF) was added, the lysate incubated on ice for 30–60 minutes, and centrifuged at 13,000×g for 20 minutes at 4° C. to pellet insoluble material. Protein concentration was determined using the micro-BCA Protein Assay Kit (Pierce Biochemicals).

Protein lysate (40 µg for Ha-ras, 5 µg for raf-1 and HER-2) was mixed with an equal volume of 2× protein sample buffer (0.05 M Tris (pH 6.8), 3% SDS, 20% Glycerol, 6% 2-Mercaptoethanol and 0.001% Bromophenol blue) boiled for 5 minutes, loaded on a 12% (5% stacking gel) SDS/Polyacrylamide gel and electrophoresed at 200 V for 8 hours. The protein was transferred to nitrocellulose membrane as previously described (Janat et al., 1994). Preparation of membrane and incubation with the primary and secondary antibodies was performed essentially as described in a protocol supplied by Santa Cruz Biotechnology, Inc., with the exception that incubation with the primary antibody was extended to 1 hour for raf-1, 2 hours for HER-2 and 4 hours for Ha-ras and wash times of 15 minutes per wash were used. The primary antibodies for HER-2 (neu C-18) and Ha-ras (ras C-20) were obtained from Santa Cruz Biotechnology, Inc. The anti-raf-1 antibody was a kind gift from Dr. Andrew Laudano, University of Vermont (McGrew et al., 1992). The washings after addition of the secondary antibody (Anti-mouse IgG-HRP, Santa Cruz Biotechnology, Inc.) were also lengthened to 15 minutes per wash.

Visualization of the protein was accomplished using the ECL Chemo-luminescent Western Blotting Kit (Amersham) according to the manufacturer's protocol.

The present invention is further detailed in the following Examples, which are offered by way of illustration and are not intended to limit the invention in any manner. Standard techniques well known in the art or the techniques specifically described below are utilized.

EXAMPLE 1

Human tumor cell lines JSQ-3 and SQ-20B, which display a high level of radiation resistance, were established from SCCHN tumors which failed radiotherapy (Weichselbaum et al., 1988; Weichselbaum et al., 1986). An activated form of the raf-1 oncogene was isolated from these cell lines via the NIH 3T3 transfection assay (Kasid et al., 1997). These and other studies with radioresistant non-cancerous skin fibroblast cell lines from a cancer-prone family (Chang et al., 1987; Pirollo et al., 1989) have clearly linked activation of raf-1 to increased RR. We, therefore, wished to determine if treatment of these cell lines with anti-raf-1 ASO would inhibit raf-1 expression and revert this phenotype. Consequently, JSQ-3 and SQ-20B were treated with increasing concentrations of anti-raf-1 oligonucleotides and the level of the raf-1 protein expression determined. Since we have previously shown that lipofectin enhanced uptake of these compounds resulting in lower effective doses, a commercially available liposome preparation (Lipofectin) was used in these and subsequent experiments (through Example 5) to facilitate delivery of the oligonucleotides. As shown in FIG. 1A, Raf-1 protein expression in JSQ-3 cells is completely inhibited by treatment with 1 µM of antisense raf-1, with significant inhibition evident at a concentration as low as 0.1 µM. The specificity of the inhibition was demonstrated by treating the cells with Lipofectin alone (0) or with a raf-1 sense oligonucleotide (S). No decrease in protein expression as compared to the untreated control cells (C) was observed in either case. A similar pattern of results was observed with cell line SQ-20B. However, with this cell line, a 3 µM concentration was necessary to effect complete inhibition of raf-1 protein, with only approximately 50% inhibition observed at 1 µM. Also shown in FIG. 1A is the effect of raf-1 ASO on a radiosensitive SCCHN cell line, SCC61. Here also treatment with raf-1 ASO was able to specifically inhibit raf-1 protein expression.

EXAMPLE 2

Figure 1B:
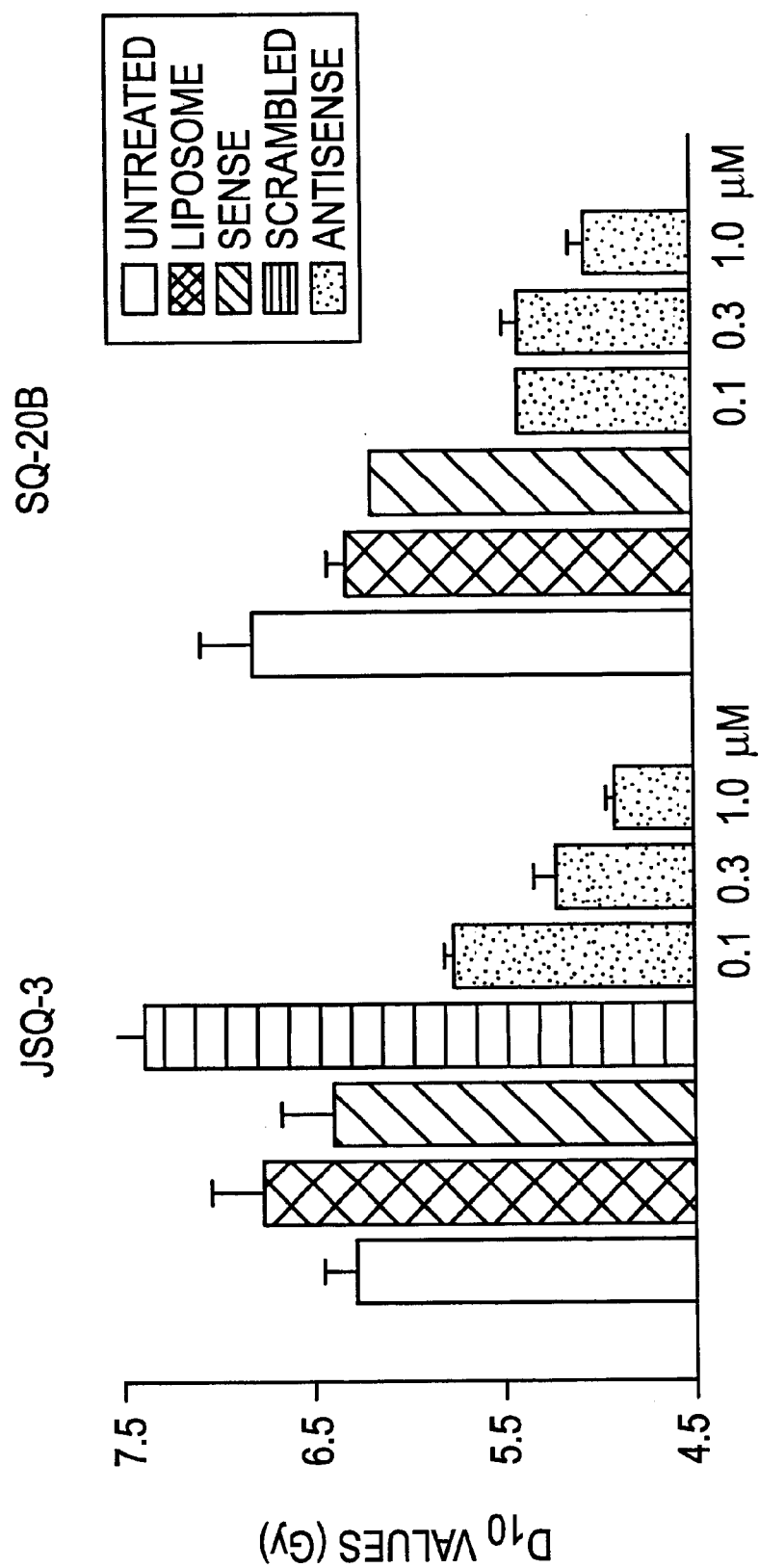

We next examined the effect of anti-raf-1 on the RR level of these cells. FIG. 1B demonstrates a dramatic increase in radiosensitivity for both cell lines after ASO treatment. This response, particularly in the JSQ-3 cells, is dose dependent. The $D_{10}$ value for JSQ-3 drops from the highly-resistant level of 6.3±0.16 Gy to 4.9±0.05 Gy, a value much closer to the level considered to be radiosensitive, after treatment with 1 µM raf-1 ASO. Even a dose as low as 0.3 µM is capable of significantly sensitizing these cells to killing by γ-radiation. Similarly, the resistance level of SQ-20B is reduced from 6.8±0.31 Gy to 5.1±0.09 Gy. This change of approximately 1.5 Gy was found to be highly statistically significant (p<0.001). Here also, the specificity of the oligonucleotide is evident since treatment with either Lipofectin (Liposome) alone, a sense, or a scrambled oligomer had minimal or no effect on the RR level of the cells. Moreover, the differences between JSQ-3 and SQ-20B with respect to their level of sensitization after ASO treatment correlates with that observed in the protein analysis, indicating that this decrease in radioresistance is directly related to Raf-1 expression. An example of the survival curves produced in these experiments is given as FIG. 3A.

By contrast, treatment of SCC61 cells, which are highly radiosensitive, with 1 µM of raf-1 ASO had no significant effect on their radiation response level. The $D_{10}$ value of the control and sense treated cells was found to be 3.3±0.4 Gy and 3.4±0.06 Gy, respectively, while that of the ASO treated was 3.0±0.4 Gy indicating a slight, but not significant, sensitization of the cells by the raf-1 ASO.

EXAMPLE 3

Figure 2:
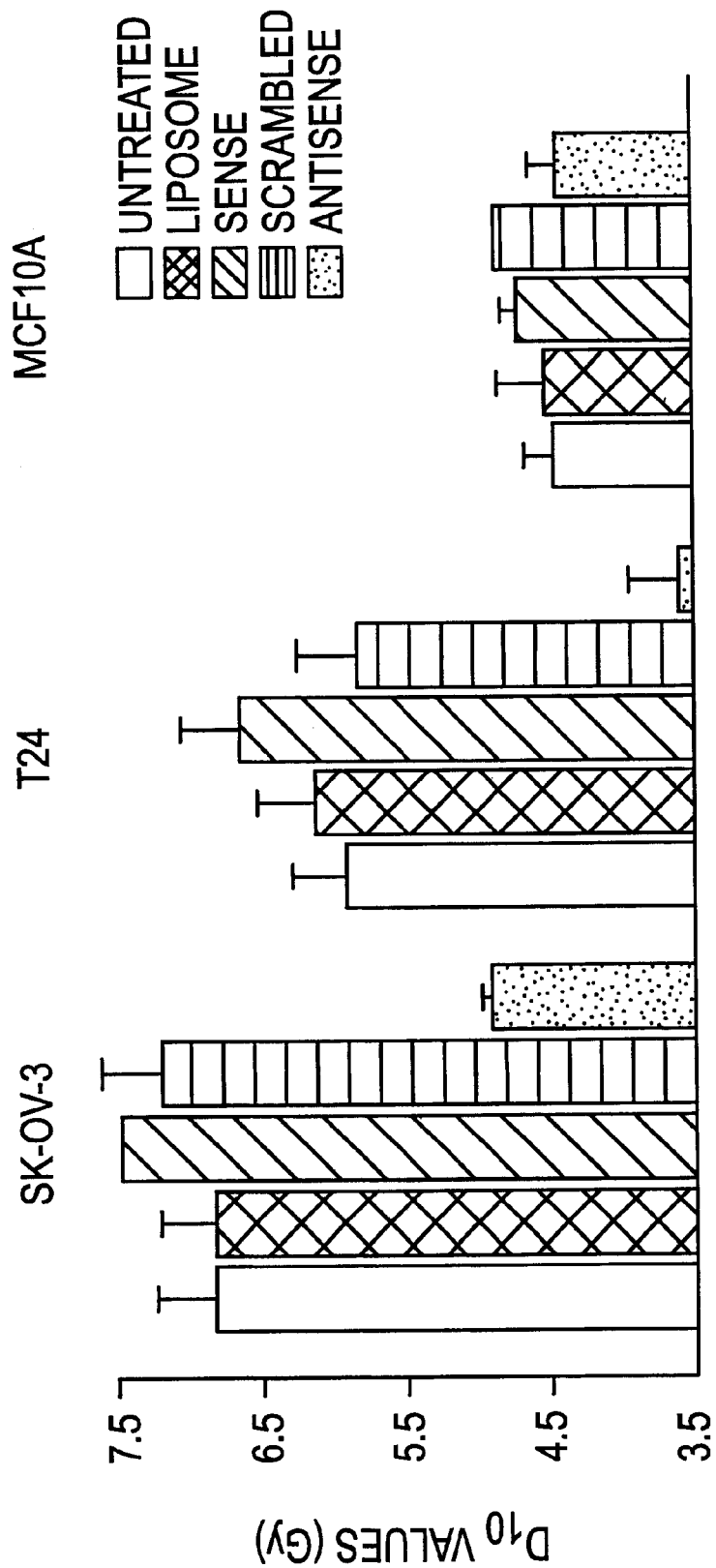
FIG. 2. Histogram demonstrating the effect of 1 $\mu$M anti-raf-1 ASO on SK-OV-3, T24 and MCF10A cells. As controls, the cells were treated with 1 $\mu$M of either a sense or a scrambled raf-1 oligonucleotide. Radioresistance levels are given as $D_{10}$ values. Error bars represent the S.E.M. of 2–6 values.
Figure 3B:
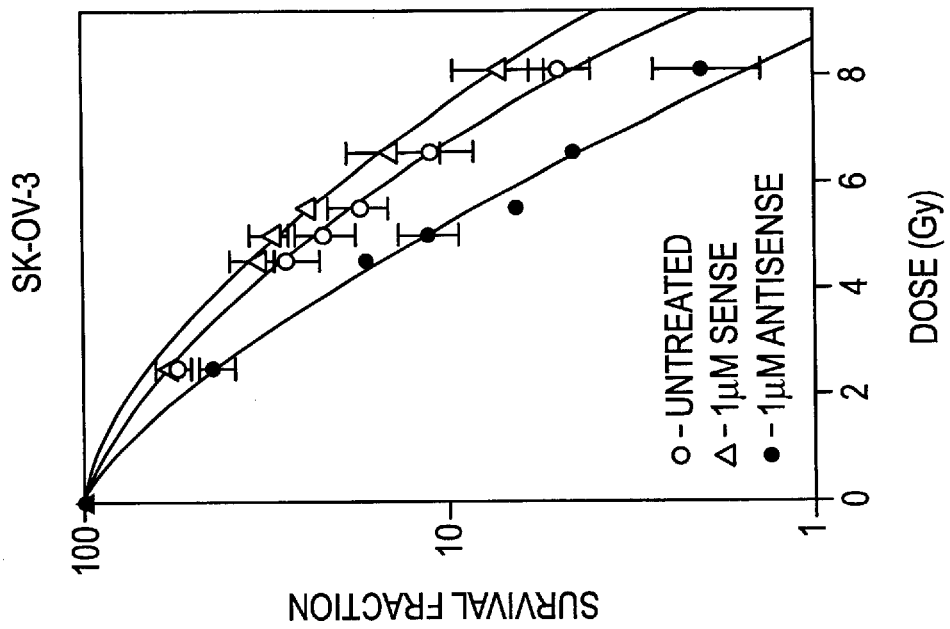
FIGS. 3A–B. Survival curves, after graded doses of $\gamma$-radiation.
Figure 3A:
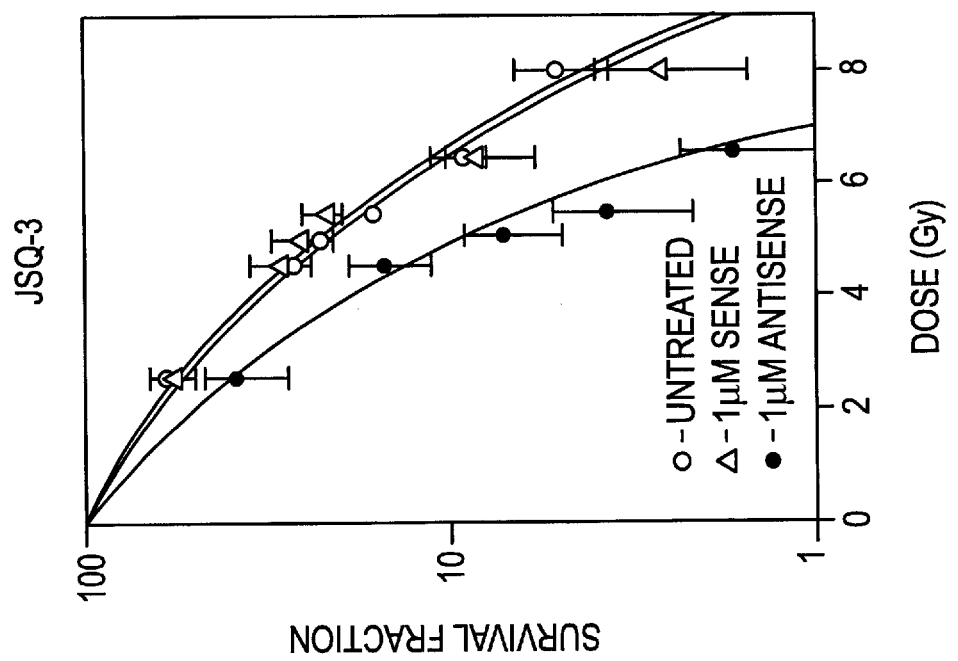

Our previous studies have placed raf-1 in a central role in a proposed signal transduction pathway leading to cellular RR. If this hypothesis is correct then treatment with raf-1 ASO of cells which have activated or abnormally expressed genes upstream of raf-1 in this pathway should block signaling leading to decreased radioresistance. Therefore, we transfected human tumor cell lines SK-OV-3 and T24 with raf-1 ASO. These two cell lines possess either elevated levels of HER-2 (Chan et al., 1995) or a mutated Ha-ras gene (Tabin et al., 1982), respectively. Both of these genes have been placed upstream of raf-1 in the signal transduction pathway (Daum et al., 1994; Rapp et al., 1988). The presence of 1 µM antisense raf-1 was able to significantly reduce the RR level of both cell lines from 6.83±0.42 Gy to 4.90±0.08 Gy for SK-OV-3 and from 5.93±0.36 Gy to 3.58±0.36 Gy for T24 (FIG. 2). As before, treatment with either the sense or scrambled oligo did not decrease on the RR level of the cells. This sensitization is also evidenced by the differences in the survival curves, between control SK-OV-3 cells, and those treated with 1 µM raf-1 antisense oligonucleotides (FIG. 3B). As a control, a normal radiosensitive breast epithelial cell line, MCF10A, was also used. As with SCC61, no effect on the $D_{10}$ values was observed with this cell line, again indicating no further sensitization of the cells at this concentration of ASO.

EXAMPLE 4

Figure 4:
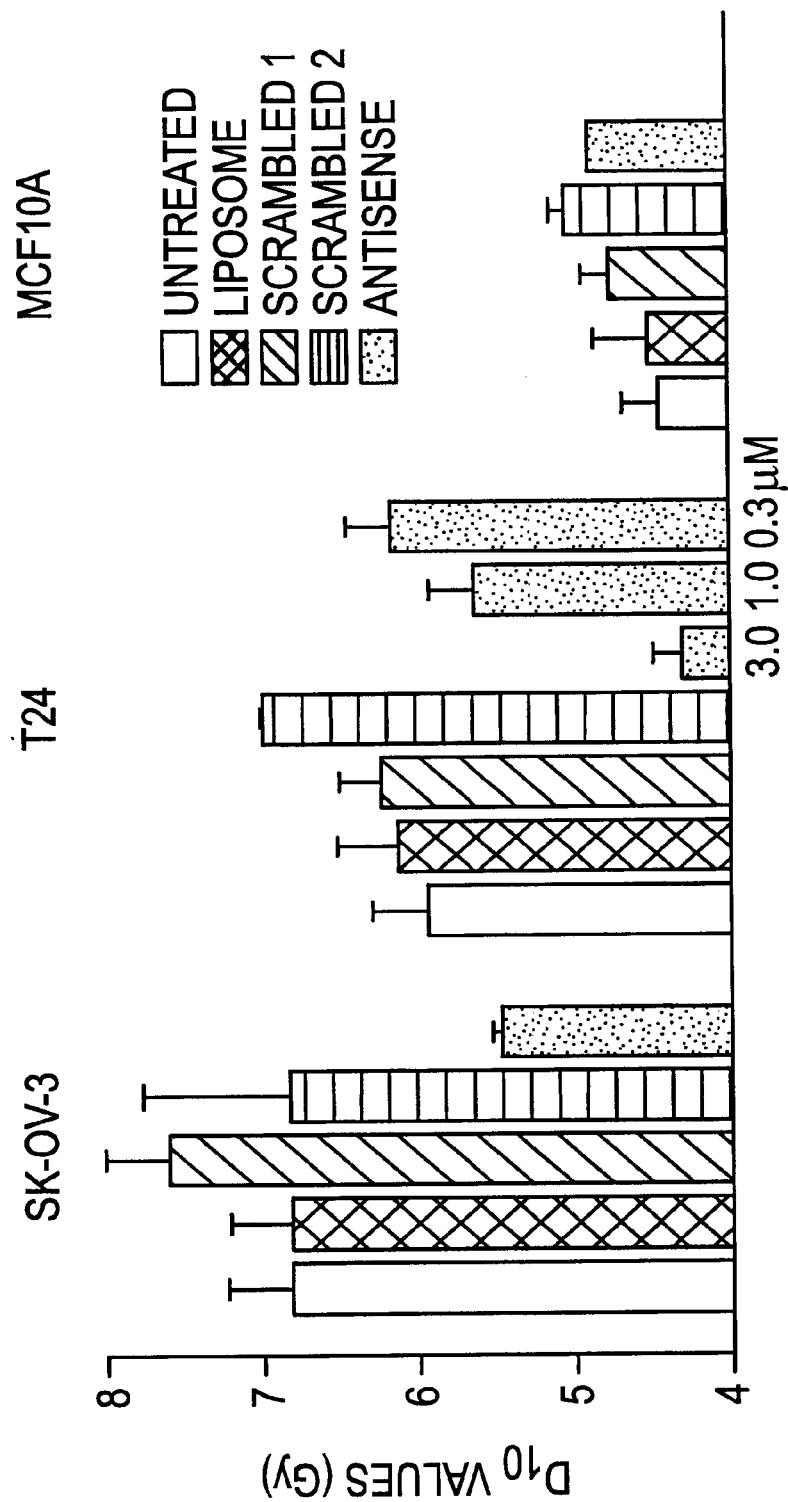
FIG. 4. Histogram demonstrating radiosensitization by Ha-ras ASO. The concentration of antisense ras oligonucleotide used to treat SK-OV-3 and MCF10A was 3 $\mu$M. As controls, the cells were treated with 3 $\mu$M of two different scrambled Ha-ras oligonucleotides. Radioresistance levels are given as $D_{10}$ values. Error bars represent the S.E.M. of 2–7 values.

To further confirm the role of these activated oncogenes in signal transduction and the RR phenotype, SK-OV-3, T24 and MCF10A cells were also treated with ASO against the Ha-ras gene. Since, as a growth factor receptor, HER-2 is upstream of ras in the proposed signaling pathway, it would be expected that the Ha-ras ASO would affect both the HER-2 expressing cells (SK-OV-3), and the cells containing mutant Ha-ras (T24). FIG. 4 shows this to be the case. $D_{10}$ for the 3 µM ASO treated T24 cells is decreased from the control value of 5.93±0.36 Gy to the significantly more radiosensitive value of 4.29±0.20 Gy, while that for SK-OV-3 is lowered from 6.83±0.42 Gy (Control) to 5.47±0.03 Gy after introduction of the anti-ras molecule. As before, there was no significant decrease in radiation survival in the control MCF10A cells after ASO treatment.

EXAMPLE 5

Figure 5A:
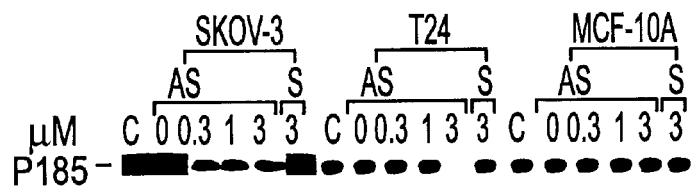
FIGS. 5A–B. The effect of anti-HER-2 oligonucleotides on p185 HER-2 protein synthesis and the radiation resistance levels of SK-OV-3, T24 and MCF10A cells.
Figure 5B:
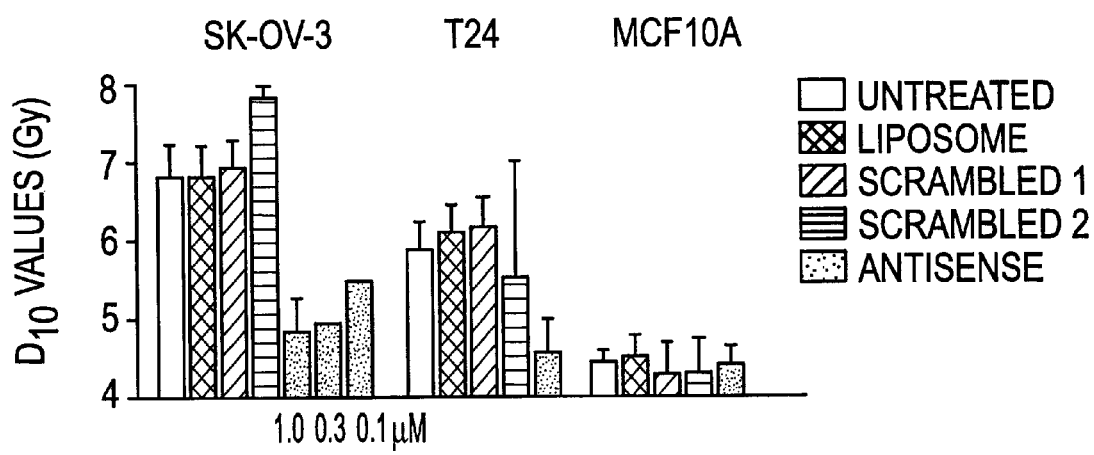
Figure 6:
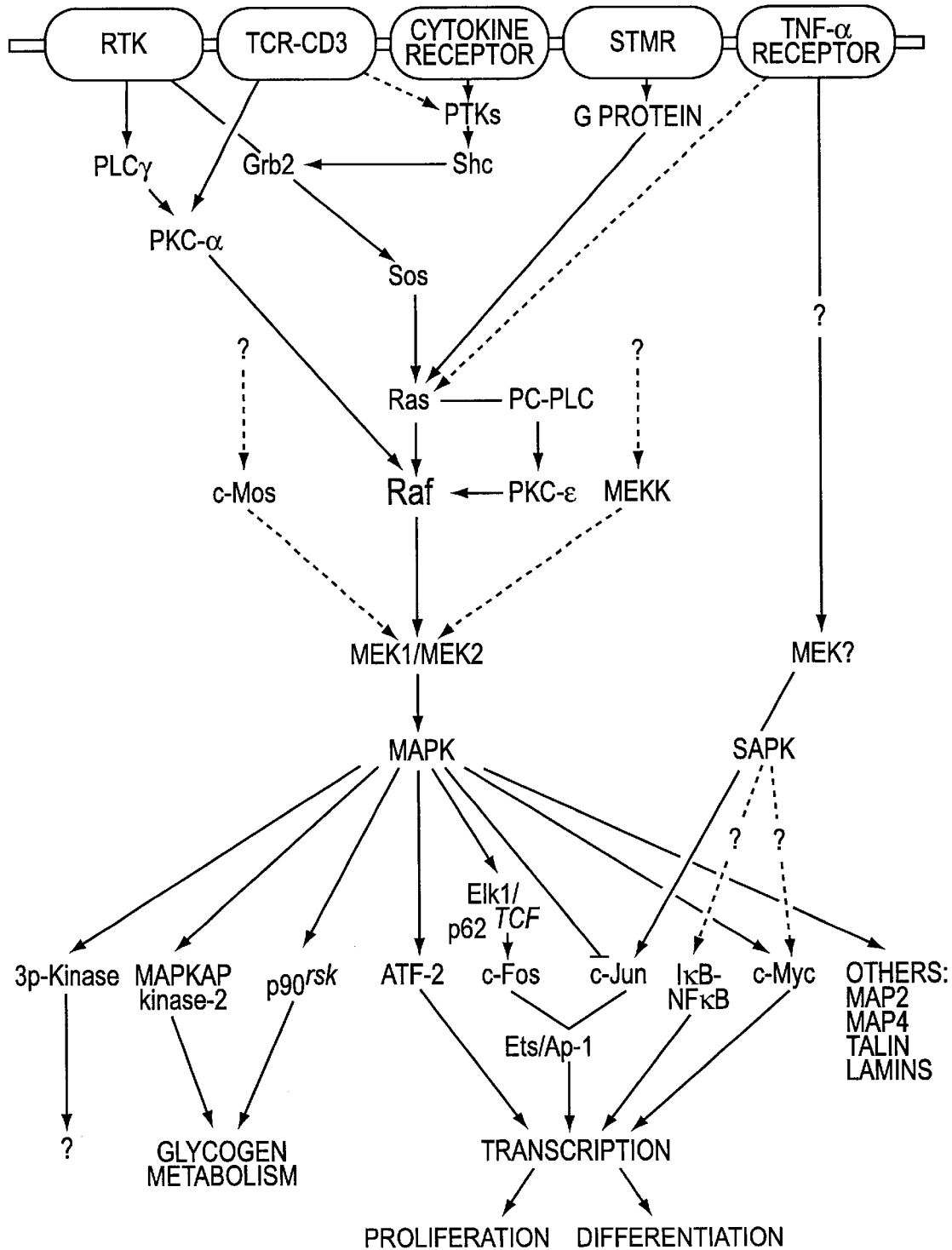
FIG. 6. Raf-dependent signal transduction. For clarity, additional pathways, such as JAK/STAT-mediated signaling, are omitted, as are feedback phosphorylation reactions. Raf is activated upon stimulation of a variety of receptors. Together with MAP/ERK kinase (MEK) and mitogen-activated protein kinase (MAPK; also known as extracellular-receptor-activated protein kinase, ERK) it forms the highly conserved cytoplasmic kinase cascade. MAPK acts on numerous effector molecules, such as other serine/threonine kinases or transcription factors, which finally determine the cellular response. Taken from Daum et al. (1994).

These same three cell lines were also treated with antisense oligonucleotides directed against HER-2. Over 80% inhibition of HER-2 protein was observed in the SK-OV-3 cells with HER-2 ASO at a concentration as low as 0.3 µM (FIG. 5A). However, significant HER-2 protein inhibition in the T24 cells is found only at 3 µM and none is evident in MCF10A, even at this relatively high concentration of ASO. The effect of HER-2 ASO on the RR level of these cells was also examined (FIG. 5B). While treatment with 0.1 and 0.3 µM HER-2 ASO had some effect on the radiosensitivity of the SK-OV-3 cells, treatment with 1 µM HER-2 ASO significantly sensitized the SK-OV-3 cells, reducing the $D_{10}$ value from 6.83±0.42 Gy to 4.88±0.43 Gy, a result virtually identical to that observed after treatment of SK-OV-3 cells with 1 µM anti-raf-1 ASO. This change of approximately 2 Gy is highly statistically significant (p<0.001) and represents a 5 fold increase in sensitivity to radiation killing these cells. Surprisingly, the radiosensitivity of the T24 cells was also altered by treatment with 1 µM HER-2 ASO.

EXAMPLE 6

Synthesis of Ligand-liposome-DNA Complexes

This example describes one method suitable for the production of the ligand-liposome-therapeutic molecule complex, where the therapeutic molecule is plasmid DNA. 15 mmol dioleoylphosphatidylethanolamine (DOPE) in dry chloroform was reacted with 20 mmol N-hydroxysuccinimide ester of folic acid (see Lee and Low, 1994), which is incorporated by reference herein for the purpose of disclosing such procedures) in the presence of 20 mmol triethylamine for 4 hours at room temperature, then washed with PBS 3 times to obtain folate-DOPE in chloroform. Thin-layer chromatography (chloroform: methanol: acetic acid, 80:20:5) revealed that more than 95% of DOPE (Rf=0.65–0.70) was converted to folate-DOPE (Rf= 0.90–0.95). LipF(A) was prepared as follows: a chloroform solution of 5 µmol dioleoyltrimethylammonium-propane (DOTAP), 5 µmol DOPE and 0.1 µmol folate-DOPE were mixed together in a round-bottom flask, and the chloroform evaporated under reduced pressure. 10 ml sterile water was added to the flask to suspend the lipids, then sonicated for 10 min in a bath-type sonicator at 4° C. The final concentration of LipF(A) was 1 nmol/µl total lipids. The LipF(A)-DNA complex for in vitro use was prepared by mixing equal volumes of LipF(A) and DNA in serum-free RPMI-1640 folate free medium (Life Technologies, Inc.) and incubating at room temperature, with frequent rocking, for 15–30 minutes. DNA retardation assay showed that at the ratio of 1 µg DNA: 8–10 nmol LipF(A), almost all of the added DNA was complexed with lipids. For in vivo experiments, plasmid DNA (diluted in HEPES buffer, pH 7.4 based upon the total amount of DNA/mouse) was mixed with LipF(A) (in water) at the ratio of 1 µg DNA/8–12 nmol lipids, and incubated for 15–30 minutes at room temperature with frequent rocking. A 50% dextrose solution was added to reach a final concentration of 5% dextrose, mixed by inversion and checked for signs of precipitation (the presence of particulate matter or cloudiness). In both cases, the LipF (A)-DNA complexes were found to be stable for up to 24 hour at 4° C. in the dark, without substantial loss of transfection efficiency.

Cationic liposomes consisting of dioleoyl trimethylammonium propane (DOTAP) and dioleoyl phosphatidylethanolamine (DOPE) (Avanti Polar Lipids, Inc., Alabaster, Ala.) were prepared as above. The final concentration of liposomes was 2 nmol/µL. Holo-transferrin (Tf, iron-saturated, Sigma) was dissolved in pure water at 5 mg/mL. The Tf-liposome-DNA complex for in vitro experiments was prepared as described by Cheng (1996) (which is incorporated herein by reference for the purpose of illustrating liposome preparation) with modifications. In brief, 12 nmol of liposomes were added to 18 mg Tf in 100 µl serum-free EMEM and incubated for 5–15 min at room temperature with frequent rocking. This solution was then mixed with 1.2 μg plasmid DNA in 100 μL serum-free EMEM and incubated for 15–30 minutes at room temperature with frequent rocking. The prepared Tf-liposome (designated LipT(A))-DNA complex was used for in vitro cell transfection freshly within 1 hour of preparation, although it was found to be stable for at least 24 hours with the same transfection efficiencies. Agarose gel electrophoresis was employed to assess the DNA retardation by LipT(A). Greater than 90% of the DNA was found to be complexed to the liposome. For in vivo studies, the liposome and transferrin (in water) were mixed and incubated for 5–15 minutes at room temperature with frequent rocking. This solution was then mixed with DNA (in HEPES buffer pH=7.4) and incubated for 15–30 minutes at room temperature with frequent rocking. A 50% dextrose solution was added to reach a final concentration of 5% dextrose, mixed by inversion and checked for signs of precipitation (the presence of particulate matter or cloudiness). In both cases, the LipT(A)-DNA complexes were found to be relatively stable for up to 24 hours at 4° C. in the dark, without substantial loss of transfection efficiency.

EXAMPLE 7

Folate-liposome Optimization by X-Gal Staining

This example describes the optimization of the folate cationic-liposome (LipF) complex of the invention for squamous cell carcinoma of the head and neck (SCCHN). To optimize the transfection efficiency for SCCHN cell line JSQ-3, the E. coli LacZ gene, driven by an SV40 promoter in plasmid pSVb, was employed as a reporter. Transfection efficiency was calculated based upon the percent of X-Gal stained cells. As shown in Table 1, the presence of folate ligand in the complex substantially increased the reporter gene expression. The non-ligand linked cationic liposome (Lip(A)) gave a transfection efficiency of 10%–20% in JSQ-3, in vitro, while LipF(A) resulted in 60%–70% of the cells expressing the β-galactosidase gene. The addition of 1 mM free folic acid to the cells prior to transfection was able to block the folate receptors on the cells, thereby reducing the transfection efficiency to 20%, similar to that observed with LipF(A). These results demonstrate that using folate as a ligand increases the transfection efficiency of cationic liposomes, and that this effect is mediated by the folate receptor. Based upon a recent report that X-gal staining may underestimate the extent of β-galactosidase gene expression by 20% or higher, it is conceivable that the transfection efficiency with the ligand-targeted liposome may actually exceed the 70% stated above.

TABLE 1

In vitro transfection efficiencies for LipF(A) in JSQ-3 cells:*

| Transfected by | Without Serum | With Serum |
| --- | --- | --- |
| PSVb alone | 0% | 0% |
| Lip(A)-pSVb | <20% | <10% |
| LipF(A)-pSVb | 60%–70% | 40%–50% |
| LipF(A)-pSVb + 1 mM Folate** | 15%–20% | 10%–20% |

*60% confluent JSQ-3 cells, cultured in folate-free medium in a 24-well plate were transfected for 5 hours with 0.5 ml of transfection solution containing 1.2 μg of pSVb. After an additional 2 days in culture, the cells were fixed and stained with X-gal. Transfection efficiency was calculated as percent of blue stained cells.
**Folate was added immediately before transfection.

EXAMPLE 8

Optimization of LipT(A) System by Luciferase Assay

This example describes the optimization of the transferrin cationic-liposome [LipT] complex of the invention for squamous cell carcinoma of the head and neck (SCCHN). The LipT(A) system was optimized for JSQ-3 transfection using the luciferase assays. The firefly luciferase gene driven by cytomegalovirus (CMV) promoter in plasmid pCMVLuc was employed as the reporter gene (Promega). $5 \times 10^4$ JSQ-3 cells/well were plated in a 24-well plate. 24 hours later, the cells were washed once with EMEM without serum, 0.3 ml EMEM without serum or antibiotics was added to each well. The freshly prepared Tf-liposome-pCMVLuc (LipT(A)-Luc) complex containing different amounts of plasmid DNA up to 1.0 μg in 0.2 ml EMEM was added to the cells. After a 5-hour incubation at 37° C. and 5% $CO_2$, 0.5 ml EMEM supplemented with 20% fetal bovine serum and 1 μ/ml hydrocortisone were added to each well. 24 hours later, the cells were washed once with PBS, lysed with 100 μl/well 1× Reporter Lysis Buffer (Promega), and the expressed luciferase activities were measured with Luciferase Assay System (Promega) on a Luminometer. A recombinant firefly luciferase (Promega) standard was used during each measurement for converting the luminometer readings of relative light unit (RLU) to the equivalent amount of luciferase expressed. Protein concentration of cell lysate was measured using the Bio-Rad DC Protein Assay Kit (Bio-Rad Laboratories). The results were expressed as μg of luciferase equivalent per mg of total protein. JSQ-3 cells were transfected with LipT(A)-pCMVLuc (LipT(A)-Luc) at different DNA/Lipid ratios in the complex. Transferrin substantially enhanced the transfection efficiency of cationic liposomes. Under optimal condition, i.e., DNA/Lipid/Tf ratio at 1 μg/10 nmol/12.5 μg, luciferase was expressed at 12.5±1.1 μg/mg total protein, or 1.25% total protein, 7- to 10-fold more than liposome alone without transferrin.

EXAMPLE 9

In Vitro Transfection of JSQ-3 Cells by LipT(A)-pSVb

This example uses a quantitative β-galactosidase colorimetric assay, as described in Example 7, to demonstrate the increased transfection efficiency of the transferrin-liposome complex of the invention. Purified β-galactosidase (Boehringer) was used as standard. The results were expressed as milliunits (mU) of β-galactosidase equivalent per mg of total protein. For histochemical studies of Tf-liposome-pSVb transfection, 60% confluent JSQ-3 cells in a 24-well plate were transfected for 5 hours with 1.2 μg of pSVb with or without LipT(A). After an additional 2 days in culture, the cells were fixed and stained with X-gal. Transfection efficiency was calculated as percentage of blue-stained cells. In quantitative β-galactosidase assay, the JSQ-3 cells transfected at the optimal condition, with 0.5 [g DNA/$10^5$ cells of LipT(A)-pSVb, expressed 15.04±0.60 mU/mg total protein of β-galactosidase without serum, and 10.95±0.15 mU/mg with serum. In histochemical studies, transfection with LipT(A)-pSVb resulted in 70%–80% of the cells being transfected. The presence of serum during transfection slightly reduced transfection efficiency, but even with serum, 40–50% of the cells stained blue, while cationic liposome without ligand gave only 10–20% efficiency. These results demonstrated that using Tf as a ligand substantially increased the transfection efficiency of cationic liposomes, even in the presence of serum.

EXAMPLE 10

Selective Tumor and Metastases Targeting by the Ligand-liposome Complex In Vivo

This example demonstrates the ability of the folate or transferrin complexed liposome to selectively target tumor tissue in vivo. Xenografts were induced by the subcutaneous injection of JSQ-3, MDA-MB-435 or DU145 cells. $2.5 \times 10^6$ (JSQ-3) or $5 \times 10^6$ (DU145) cells were injected on the lower back above the tail of 4–6 week old female athymic nude (NCr nu-nu) mice. $1 \times 10^7$ MDA-MB-435 cells were injected subcutaneously into the mammary fat pad of the mice. For the metastases model, $1 \times 10^6$ JSQ-3 or MDA-MB435 cells were intravenously injected, via the tail vein, into the animals. LipF(A)-pSVb or LipF(D)-pSVb was prepared as described in Example 6. LipF-pSVb or pSVb plasmid alone (in 5% dextrose) were injected intravenously via the tail vein, at 25 μg of plasmid DNA/300 μl/animal. Two days and 10 days after DNA injection, the tumors as well as mouse organs were excised, cut into 1 mm sections, washed once with PBS, and fixed with 2% Formaldehyde-0.2% glutaraldehyde for 4 hours at room temperature. The fixed tumor sections were washed 4 times, each for 1 hr, and stained with X-Gal solution plus 0.1% NP-40 (pH 8.5) at 37° C. overnight. The stained tumor sections were embedded and sectioned using normal histological procedures and counterstained with nuclear fast red. Four sections per tumor were examined to evaluate the β-galactosidase gene expression, as indicated by the blue stained cells. LipF(A)-pSVb or pSVb alone was intravenously injected into nude mice bearing JSQ-3 xenografts. Within 48 hours, the LipF(A)-pSVb injected group showed reporter gene expression in the tumors with an in vivo transfection efficiency of approximately 40–50%. In contrast, with pSVb plasmid alone, less than 1% of the tumor cells stained for the β-galactosidase reporter gene. Ten days after i.v. administration of LipF(A)-pSVb, both the percentage and intensity of blue staining in the tumors were substantially reduced, indicating that the LipF(A)-mediated systemic transfection is transient. Vital organs in LipF(A)-pSVb injected mice showed only macrophages such as Kupffer cells (liver) or dust cells (lung) staining blue, while the hepatocytes and lung alveoli cells themselves remained unstained. The selectivity of tumor targeting was also shown where the tumor was found invading muscle. The LipF(A)-pSVb transfected only the tumor while the muscle cells remained unstained. More significantly, the highly proliferating bone marrow and intestinal crypt cells were apparently not transfected. Both the crypt cells and the bone marrow showed little if any (<1%) evidence of reporter gene staining. The lack of LipF(A)-pSVb transfection in the bone marrow and crypt cells demonstrates that targeting is not a nonselective, cell proliferation effect, but appears to be targeting the tumor cells. This is further demonstrated by no staining being evident in the endothelial cells of blood vessels, although they were exposed to the highest concentration of the LipF(A)-pSVb complex as it travels through the blood stream. In addition, no staining was evident in the lymphoblastic growth centers in the spleen even though the dendritic cells displayed B-galactosidase staining.

A major problem in cancer recurrence and treatment is metastases. To test for the ability of the LipF(A) complex to target tumor cells apart from the subcutaneous xenograft, JSQ-3 cells were i.v. injected into nude mice. By two weeks after the injection, simulated metastases (islands of tumor cells in multiple organs) formed Animals were then injected intravenously with LipF-pSVb and the simulated metastases examined for β-galactosidase expression. Extensive X-gal staining was seen in a metastasis found in a thoracic lymph node. In this section, a blood vessel (BV) was found surrounded by the metastatic tumor cells. Although the tumor cells exhibited strong X-gal staining 20–25 layers from the blood vessel, no reporter gene expression was evident in the endothelial cells of the blood vessel, even though they were exposed to the highest concentration of the LipF(A)-pSVb complex as it traveled through the blood stream. These results confirmed the tumor-selective nature of the LipF(A) complex and demonstrated that metastases as well as primary tumors can be targeted via folate-containing liposomes.

To assess the breadth of applicability this folate-linked, liposome mediated delivery system to cancers other than SCCHN, experiments were also performed with xenografts of other human tumor cell lines including human breast carcinoma cell lines MDA-MB-435, Hs578T, and human prostate cancer cell line DU145, which also carry mt p53. Here too, a single i.v. injection of LipF(A)-pSVb demonstrated tumor selectivity. A high level of β-galactosidase expression was seen in the MDA-MB-435 mammary fat pad tumor while the adjacent normal muscle tissue remained unstained. Reporter gene expression was not detected in non-tumor tissues or normal organs including intestinal crypt cells and hepatocytes, while subcutaneous mammary fad pad xenografts showed an average of 50–70% blue staining. Two weeks after i.v. injection of MDA-MB-435 cells, the LipF(A)-pSVb was systemically delivered via a single tail vein injection. Even small simulated breast metastases in the lung displayed a high level of staining, and the adjacent normal lung tissue remained completely unstained.

Mice bearing DU145 xenografts were given a single i.v. injection of LipF(B)pSVb. Tumors in these mice also showed reporter gene expression representing an in vivo transfection efficiency of at least 40–50%, a value about 50-fold higher than achieved with plasmid alone.

The transferrin-liposome, liposome-pSVb and pSVb DNA complexes were prepared in sterile 5% dextrose instead of HBSS, at a ratio of 1 μg DNA/10 nmol liposome/12.5 μg transferrin. The nude mouse tumor model was established by subcutaneous injection of JSQ-3 cells in the flank of 4–6 weeks old female nude mice. 30 μg pSVb DNA complexed with Tf-liposome in 300 ml volume were injected into each mouse via tail vein with 1 cc syringe and a 30 G needle. In the control groups, liposome-pSVb or pSVb DNA without liposome were injected. At 2 days, the tumors in mice injected with LipT(A)-pSVb showed reporter gene expression representing an in vivo transfection efficiency of approximately 20–40%. In contrast, with pSVb plasmid alone, without liposome, less than 1% of the tumor cells stained for reporter gene expression. Ten days after intravenous administration of LipT(A)-pSVb, both the percentage of positive cells and the intensity of blue staining in the tumors were substantially reduced, indicating that the LipT(A)-mediated systemic transfection was transient. Vital organs in mice injected with LipT(A)-pSVb showed staining of only macrophages (such as dust cells of the lung and Kupffer cells of the liver), whereas the hepatocytes and lung alveolar cells remained unstained. No staining was evident in the lymphoblastic growth centers in the spleen although the dendritic cells displayed modest staining. In summary, the histological staining indicated that delivery of the reporter gene by LipT(A) was selective with the human xenograft being most heavily stained.

EXAMPLE 11

Optimization of Ligand-liposome Transfection in Different Cancer Cell Lines

In this example we further explored the ligand-cationic liposome system, preparing a panel of ligand-targeted cationic liposomes to optimize the transfection efficiency to a variety of human and rodent cancer cells.

Cationic liposomes were prepared as follows:

| LipA DOTAP/DOPE | 1:1 molar ratio |
| LipB DDAB/DOPE | 1:1 molar ratio |
| LipC DDAB/DOPE | 1:2 molar ratio |
| LipD DOTAP/Chol | 1:1 molar ratio |
| LipE DDAB/Chol | 1:1 molar ratio |
| LipG DOTAP/DOPE/Chol | 2:1:1 molar ratio |
| LipH DDAB/DOPE/Chol | 2:1:1 molar ratio |

1. Folate series: Each of the above formulations plus 1%–5% folate-DOPE or folate-DSPE.

2. Transferrin series: Each of the above formulations mixed with holo-transferrin in medium or buffer, then mixed with reporter gene plasmid DNA in medium or buffer to form the complex.

The firefly luciferase gene in plasmid pCMVLuc or $E.\ coli$ β-galactosidase gene in plasmid pCMVb was used as a reporter gene.

Preparation of DNA-liposome Complexes:

The various DNA-Liposome-Folate complexes was prepared by mixing, in polypropylene tubes, equal amounts of serum-free medium and the reporter gene plasmid DNA in TE buffer (10 mM Tris-HCl, 1 mM EDTA, pH 8.0), and equal amounts of serum-free medium with the folate-liposome (LipA-F, LipB-F, LipC-F, LipD-F, LipE-F, LipG-F, LipH-F) in sterile water (2 μmol/ml total lipids). After 10–15 min at room temperature, the two solutions were mixed together and incubated 15–30 min at room temperature with frequent rocking. The DNA to lipid ratios in optimization ranged from 1:0.1 to 1:50 μg/nmol.

The various DNA-Liposome-Transferrin complexes were prepared by the addition of Tf (iron-saturated, Sigma, 4–5 mg/ml in water, filtered with 0.22 mm filter) to serum-free medium. 5–15 min later, cationic liposome (LipA, LipB, LipC, LipD, LipE, LipG, LipH) was added and mixed. After 5–15 min. incubation at room temperature with frequent rocking, an equal amount of medium containing reporter gene plasmid DNA was added and mixed, and incubated 15–30 min at room temperature with frequent rocking. The DNA/Lipid/Tf ratios in optimization were in the range of 1/(0.1–50)/(0.1–100) μg/nmol/μg.

Cell Lines:

Optimization was performed on the following cell lines:

Human squamous cell carcinoma of head and neck: JSQ-3, HN17B, HN22a, HN-38, SCC-25.

Human breast cancer: MDA-MB-231, MDA-MB-435, MDA-MB-453, MCF-7.

Human prostate cancer: DU145, LNCaP, Ln-30, P4–20.

Human ovary cancer: SKOV-3, PA-1

Human pancreatic cancer: PANC-1

Human colon cancer: SW480, LS174T, SK-CO-1

Human glioblastoma: U-87

Human cervical cancer: HTB-34, ME180

Human lung cancer: CALU-3

Human gastric cancer: Hs 746T

Human liposarcoma: SW 872

Human melanoma: SK-MEL-31

Human choriocarcinoma: JEG-3

Human rhabdomyosarcoma: Hs 729T

Human retinoblastoma: Y79

Human normal breast epithelial: Hs578Bst

Human endothelial: HUV-EC-C

Mouse melanoma: B16/F10

Rat prostate cancer: PA-III, AT.61

Rat brain cancer: RT-2

Optimization by Luciferase Assay $5 \times 10^4$ cells/well were plated in a 24-well plate. 24 hours later, the cells were washed once with medium without serum, 0.3 ml medium without serum and antibiotics was added to each well. The freshly prepared LipT-pCMVLuc or LipF-pCMVLuc complexes containing different amounts of plasmid DNA (up to 1.0 μg in 0.2 ml) medium was added to the cells. After a 5-hour incubation at 37° C. and 5% $CO_2$, 0.5 ml medium supplemented with 20% fetal bovine serum was added to each well. 24 hours later, the cells were washed once with PBS, lysed with 100 μ/well 1× Reporter Lysis Buffer (Promega), and the expressed luciferase activities were measured with Luciferase Assay System (Promega) on a Luminometer. The protein concentration of the cell lysate was measured using the Bio-Rad DC Protein Assay Kit (Bio-Rad Laboratories). The results were expressed as relative light unit (RLU) per μg of total protein.

Optimization by β-Galactosidase Colorimetric Assay $1 \times 10^4$ cells were plated in each well of a 96-well plate or $5 \times 10^4$ cells/well in 24-well plate. 24 hours later, the cells were washed once with medium without serum or antibiotics and 100 μl transfection solution containing various amounts of LipT-pCMVb, LipF-pCMVb, or pCMVb alone, were added to each well. After 5 hours at 37° C., an equal amount of medium containing 20% fetal bovine serum was added to each well. 48 hours later, the cells were washed once with PBS, and lysed in 1× reporter lysis buffer (Promega). The cell lysates were treated with 100 μl 150 μM 0-nitrophenyl-β-galactopyranoside in 20 mM Tris (pH 7.5) containing 1 mM $MgCl_2$ and 450 μM β-mercaptoethanol at 37° C. for 0.5 hour. The reaction was stopped by the addition of 150 μl/well of 1 M $Na_2CO_3$. The absorbancy was determined at 405 nm. Purified β-galactosidase (Boehringer) was used as standard. The results were expressed as milli-unit of β-galactosidase equivalent per μg of total protein.

Histochemical Staining:

For histochemical studies of ligand-liposome-pCMVb transfection, cells at 60% confluence (in a 24-well plate) were transfected for 5 hours as described above. After an additional 2 days in culture, the cells were fixed and stained with X-gal. Transfection efficiency was calculated as percentage of blue-stained cells. Transfection efficiencies of the different liposome compositions with different cell lines:

As shown in Table 2, LipT(A) and LipT(D) demonstrated the highest transfection efficiency for JSQ-3 cells, 3–8 fold more efficient than other liposome formulations. LipT(D) was the most efficient for both MDA-MB-435 and DU145. At the ratio of 1/12/15 (DNA μg/Lip nmol/Tf μg) or higher, LipT(D) gave high efficiency to JSQ-3 and LipT(A) to MDA-MB-435 cells, but cytotoxicity became obvious. More importantly, when preparing Tf-Lip-DNA complexes for in vivo experiments, the complex at this ratio or higher (lipids) tends to precipitate, the solution of the complex tends to become cloudy (i.e., not as clear as solutions prepared at lower ratios) and not stable. Therefore, the preferred ratio of LipT is 1/10/12.5 (DNA μg/Lip nmol/Tf μg).

TABLE 2

| Liposomes | Ratio** | DU145 | MDA-MB435 | JSQ-3 |
|---|---|---|---|---|
| LipT(A) | 1/6/7.5 | 0.62 | 1.18 | 24.62 |
|  | 1/8/10 | 1.54 | 2.90 | 76.07 |
|  | 1/10/12.5 | 3.05 | 2.32 | 117.64 |
|  | 1/12/15 | 1.50 | 14.56 | 81.09 |
| LipT(B) | 1/6/7.5 | 1.06 | 6.35 | 44.11 |
|  | 1/8/10 | 0.97 | 5.91 | 36.45 |
|  | 1/10/12.5 | 0.78 | N/A | 43.00 |
|  | 1/12/15 | 0.28 | 5.90 | 38.98 |
| LipT(C) | 1/6/7.5 | 0.043 | 0.66 | 2.80 |
|  | 1/8/10 | 0.087 | 1.63 | 7.35 |
|  | 1/10/12.5 | 0.33 | 2.59 | 16.59 |
|  | 1/12/15 | 0.25 | 3.48 | 17.29 |
| LipT(D) | 1/6/75 | 0.076 | 4.00 | 1.88 |
|  | 1/8/10 | 0.26 | 7.43 | 3.43 |
|  | 1/10/12.5 | 0.92 | 9.63 | 42.20 |
|  | 1/12/15 | 3.06 | 13.44 | 124.60 |
| LipT(E) | 1/6/7.5 | 0.54 | 7.56 | 9.46 |
|  | 1/8/10 | 0.87 | 5.31 | 8.96 |
|  | 1/10/12.5 | 1.12 | 4.52 | 20.91 |
|  | 1/12/15 | 1.33 | 6.21 | 27.95 |
| Plasmid |  | 0.0001 | 0.0034 | 0.0001 |

*×$10^6$ RLU/mg protein
**Ratios of DNA μg/Lip nmol/Tf μg

Similar to transferrin, LipF(A) and LipF(C) provided the best results for JSQ-3 cells, 2 to 8-fold more efficient than other liposome formulations (Table 3). Interestingly, folate-liposomes give totally different patterns of efficiencies compared with Tf-liposomes in both MDA-MB-435 and DU145 cells, and in other cell lines as well. LipF(C) provided the best results for MDA-MB-435 and LipF(E) provided the best results for DU145 (Table 3). Similar results with less efficiency were obtained in some cancer cell lines transfected with liposomes of DOTMA/DOPE 1:1 and 1:2 molar ratios.

TABLE 3

| Liposomes |  | DU145 0.25 μg DNA | DU145 0.5 μg DNA | MDA-MB-435 0.5 μg DNA | JSQ-3 0.5 μg DNA |
|---|---|---|---|---|---|
| LipF(A) | 1/6** | 0.05 |  |  |  |
|  | 1/8 | 0.31 | 0.58 | 2.16 | 76.90 |
|  | 1/10 | 0.16 | 0.29 | 0.59 | 77.96 |
|  | 1/12 | 0.18 |  |  |  |
| LipF(B) | 1/6 | 0.42 |  |  |  |
|  | 1/8 | 1.27 | 2.68 | 2.26 | 44.80 |
|  | 1/10 | 1.03 | 1.94 | 1.71 | 42.15 |
|  | 1/12 | 1.61 |  |  |  |
| LipF(C) | 1/6 | 0.10 |  |  |  |
|  | 1/8 | 0.44 | 1.14 | 3.58 | 36.27 |
|  | 1/10 | 0.54 | 1.15 | 1.62 | 83.88 |
|  | 1/12 | 0.35 |  |  |  |
| LipF(D) | 1/6 | 0.05 |  |  |  |
|  | 1/8 | 0.05 | 0.53 | 1.07 | 25.95 |
|  | 1/10 | 0.38 | 0.74 | 0.64 | 34.47 |
|  | 1/12 | 0.20 |  |  |  |
| Lip(E) | 1/6 | 2.71 |  |  |  |
|  | 1/8 | 2.08 | 2.23 | 0.98 | 12.12 |
|  | 1/10 | 1.63 | 2.95 | 1.07 | 23.91 |
|  | 1/12 | 1.60 |  |  |  |
| Plasmid |  | 0.27 × $10^{-6}$ | 0.13 × $10^{-3}$ | 0 | 0 |

*+$10^6$ RLU/mg protein
**Ratios: DNA μg/Lip nmol

Table 4 shows the preferred ligand-liposome formulations for some of the cell lines we have tested in vitro using the ligand-liposome system disclosed in the invention. It should be noted that the optimal compositions for in vitro transfection are not necessarily the optimal ones for in vivo transfection. But it tends to be that the in vitro preferred compositions are a good starting point leading to the preferred compositions for in vivo. Therefore, in vivo optimization using nude mouse xenograft models is necessary before the in vivo systemic gene therapy experiments, as disclosed in the invention.

TABLE 4

| Cell Line | Tf-liposome | Folate-liposome |
|---|---|---|
| JSQ-3 | LipT(A),(D) | LipF(A),(C) |
| HN 17B | LipT(B) |  |
| HN 22a | LipT(A) |  |
| HN 38 | LipT(B) |  |
| SCC-25 | LipT(A) |  |
| SCC-25cp | LipT(A) |  |
| MDA-MB-231 | LipT(E) |  |
| MDA-MB-435 | LipT(D),(A) | LipF(C),(B) |
| MDA-MB-453 | LipT(C) |  |
| DU 145 | LipT(D),(H) | LipF(E) |
| P4-20 | LipT(A) |  |
| SKOV-3 | LipT(D),(B) |  |
| PA-1 | LipT(A) |  |
| PANC-1 | LipT(D),(H) | LipF(D),(A) |
| SW 480 | LipT(A) |  |
| LS 174T |  | LipF(D) |
| SK-CO-1 |  | LipF(E) |
| U-87 | LipT(D),(A) |  |
| HTB-34 | LipT(C),(A) | LipF(C) |
| ME 180 |  | LipF(E) |
| CALU-3 |  | LipF(D) |
| HS 746T |  | LipF(E) |
| HS 578 Bst |  | LipF(E) |
| HUV-EC-C |  | LipF(E) |
| B16 F10 | LipT(A),(C) | LipF(E) |
| JEG-3 |  | LipF(B) |
| HS 729T |  | LipF(B) |
| Y79 |  | LipF(D) |
| PA-III |  | LipF(C),(H) |
| AT6.1 | LipT(H) | LipF(H) |
| RT-2 |  | LipF(B) |

Effect of Serum on the Transfection Efficiency of Ligand-liposomes

LipT(D) had the highest level of transfection efficiency with human glioblastoma cell line U-87 without serum. However, in the presence of 10% serum its transfection efficiency was substantially reduced, while LipT(A) was most efficient in the presence of serum for this cell line. For human pancreatic cancer cell line PANC-1, serum appeared to enhance the transfection with some liposome compositions, with LipT(H) displaying the highest level of efficiency. Here again, we observed different transfection efficiency patterns in different cell lines, and different effects of serum on transfection efficiency. For the purpose of in vivo transfection, serum effects should be considered during optimization.

EXAMPLE 12

Stability of LipF(B)-AS-HER-2 In Vitro and in Blood

As a goal of these studies was to develop a systemic delivery system for antisense oligonucleotides, it was important to determine the stability of the LipF(B)AS-HER-2 complex in serum. Therefore, the complex was added to 50% serum and incubated at 37° C. At various times from 0–24 hours, samples were taken, the oligonucleotides labeled with $^{32}$P and percent degradation assessed by PAGE. No degradation of the AS-HER-2 oligonucleotide was found when complexed to LipF(B) for 24 hours. In contrast, over 50% of the free oligonucleotide was degraded as early as 6 hours, with virtually complete degradation by 24 hours.

The stability was also examined in mouse blood, a setting more analogous to the in vivo situation. Even after 24 hours, more than 75% of the complexed oligonucleotide remained intact. Therefore, it was concluded that the folate targeted delivery system should protect the oligonucleotide long enough in circulation to allow it to effectively reach the tumor cells.

EXAMPLE 13

Chemosensitization of Tumor Cells by Ligand-targeted, Liposome-mediated Antisense Oligonucleotides In Vitro and In Vivo This example demonstrates the ability of the systemically administered ligand-liposome-therapeutic molecule delivery system of the invention to deliver small oligonucleotides as the therapeutic molecule. Further, this example demonstrates the ability of the systemically administered, ligand-liposome-delivery of the small oligonucleotides to sensitize the contacted tumor cells to chemotherapeutic agents.
Optimization of the Folate-liposome (LipF) Composition for Various Tumor Cell Types:

Starting with the ligand-liposome complex derived for SCCHN cell lines and described above, further ligand-liposome compositions optimized for delivering anti-sense HER-2 (AS-HER-2) oligonucleotides to tumor cells were developed. The AS-HER-2 oligonucleotide was SEQ ID NO:3 which is a 15-mer complementary to a sequence near the initiation codon of the HER-2 gene (Pirollo et al., 1997).
Saturation of Liposomes by Oligonucleotides:

Multiple new folate-liposomes (LipF) compositions were produced by varying the cationic and neutral lipid in the complex. Helper lipids were also included in some compositions. The ratio of cationic to neutral lipid was also varied. Using $^{32}$P-labeled AS-HER-2 oligonucleotide, we determined the ratio of liposome to oligonucleotide that gave optimal binding of the oligonucleotide to the various compositions. An example of these studies is shown in Table 5 where a comparison is made between LipF compositions B and C versus Liposome A, which is the LipF composition optimized for SCCHN.

TABLE 5

| Ratio<br>Lip:Oligo | Liposome<br>A | Liposome<br>B | Liposome<br>C |
|---|---|---|---|
| 1:10 | 23% | 51.6% | 44.25% |
| 1:1 | 87.7% | 77.9% | 61.97% |
| 5:1 | 90% | 90.7% | 72.6% |
| 10:1 | 93% | 98% | 86.7% |
| 25:1 | 100% | 100% | 100% |

There is clearly a difference in the oligonucleotide binding between the three compositions. Nevertheless, complete saturation is achieved with all three at a liposome:oligonucleotide ratio of 25:1. However, a substantial amount of toxicity was evident at this ratio. It is also evident from these data that for different liposome compositions, the optimal ratio is dramatically different.
AS-HER-2 oligonucleotide Uptake by Tumor Cell Lines with Various LipF Compositions:

Transfection experiments were performed with the LipF compositions and human breast cancer cell line MDA-MB-435, SCCHN cell line JSQ-3, prostate tumor cell line DU145 and pancreatic tumor cell line PANC 1, to determine the transfection efficiency of each LipF composition. Those used were the four compositions (designated B–E) which were found to have the most efficient binding of the oligonucleotide. The two molar ratios of Liposome:Oligonucleotide used initially in these studies were 10:1 and 25:1, those found (see above) to possess the highest oligonucleotide binding levels. However, a ratio of 25:1 was found to be toxic to the cells. Therefore, the remainder of the experiments were performed using a ratio of 10:1 (liposome:oligonucleotide). Transfections, using $^{32}$P labeled AS-HER-2, were performed as previously described for LipF(A)-p53 for SCCHN. However, after twenty hours incubation at 37° C., the media was removed and the cells washed five times with PBS. The media and washes were combined and the amount of unincorporated label ascertained. The amount of cell associated $^{32}$P-labeled anti-HER-2 oligonucleotide was determined by comparing the $^{32}$P level within the cells versus the unincorporated oligonucleotide. In these studies LipF(A) is the composition originally optimized for SCCHN. As shown in Table 6, LipF composition B yielded the highest level of transfection efficiency in MDA-MB-435 breast cancer cells, while LipF composition E was better for both DU145 and PANC I. Therefore, LipF composition B [LipF(B)] was used for the remainder of the studies with MDA-MB-435, described below.

TABLE 6

| CELL<br>LINE | Liposome<br>A | Liposome<br>B | Liposome<br>C | Liposome<br>D | Liposome<br>E |
|---|---|---|---|---|---|
| MDA-MB-435 | 112 | 280 | 108 | 242 | 137 |
| JSQ-3 | 184 | 100 | 8 | 125 | 205 |
| DU145 | 93 | 158 | 130 | 403 | 705 |
| PANC1 | 330 | 490 | 407 | 398 | 731 |

Oligonucleotide concentration was 2 μM
Molar ratio of Liposomes:Oligonucleotide was 10:1
In Vitro Chemosensitization of Cancer Cells by LipF-AS-HER-2

The ability of the LipF(B)-delivered AS-HER-2 to sensitize MDA-MB435, JSQ-3, DU145 and U87 (Human glioblastoma) cells to chemotherapeutic agents was evaluated. Sensitivity was determined using the XTT cell proliferation assay. Transfection with LipF(B)-AS-HER-2 substantially increased the killing effect of docetaxel upon the 435 cells. Comparison of the cells treated with LipF(B) mediated AS-HER-2, to that of cells treated with a LipF(B) control oligonucleotide (SC) indicated a greater than 30 fold increase in sensitization of 435 cells to taxotere. In contrast, only a 2.5 fold level of sensitization was evident after transfection with AS-HER-2 using the commercial Lipofectin (Life Technologies, Inc.). Treatment of JSQ-3 cells with LipF(E)AS-HER-2 increased the effect of docetaxel almost 25 fold. Moreover, the effect of cisplatin (CDDP) on JSQ-3 cells was also increased by greater than 17 fold after treatment with AS-HER-2 complexed to transferrin-targeted Liposome A (LipT(A)). A two fold increase in sensitization of DU145 cells to docetaxel was seen after treatment with LipF(E)-AS-HER-2. Human glioblastoma cell line U87 showed a greater than 8 fold increase in chemosensitivity to the drug gemcitabine after treatment with LipF(B)-AS-HER-2.

To further demonstrate the use of the targeted liposome complex as a vector for antisense gene therapy delivery, the ability of LipF(B) carrying an anti-RAS oligonucleotide (AS-RAS, an 11 mer sequence complementary to the sequence near the initiation codon of the gene) to sensitize PANC I pancreatic carcinoma cells to docetaxel was examined. Here also a greater than 70 fold increase in drug sensitivity was induced by treatment with LipF(B)-AS-RAS. The data showed that LipF(B)- mediated antisense gene therapy can lead to a substantial increase in the effectiveness of chemotherapeutic agents in previously resistant human cancer cells.

In Vivo Studies

The ability of the LipF(B)-AS-HER-2 to target and sensitize preexisting MDA-MB435 xenograft tumors to the chemotherapeutic agent docetaxel in vivo was examined by assessing tumor regression as well as tumor growth inhibition. Female athymic (Ncr nu/nu) mice carrying MDA-MB435 mammary fat pad xenograft tumors of approximately 70 mm$^3$ were intravenously injected, via the tail vein, with LipF(B)-AS-HER-2 (20 nanomoles of antisense oligonucleotide in 400 µL of total liposome complex) every other day to a total of 11 injections. A total of 11 intravenous doses of docetaxel (approximately 20 mg/kg/dose every other day) were also administered to the animals.

Figure 7:
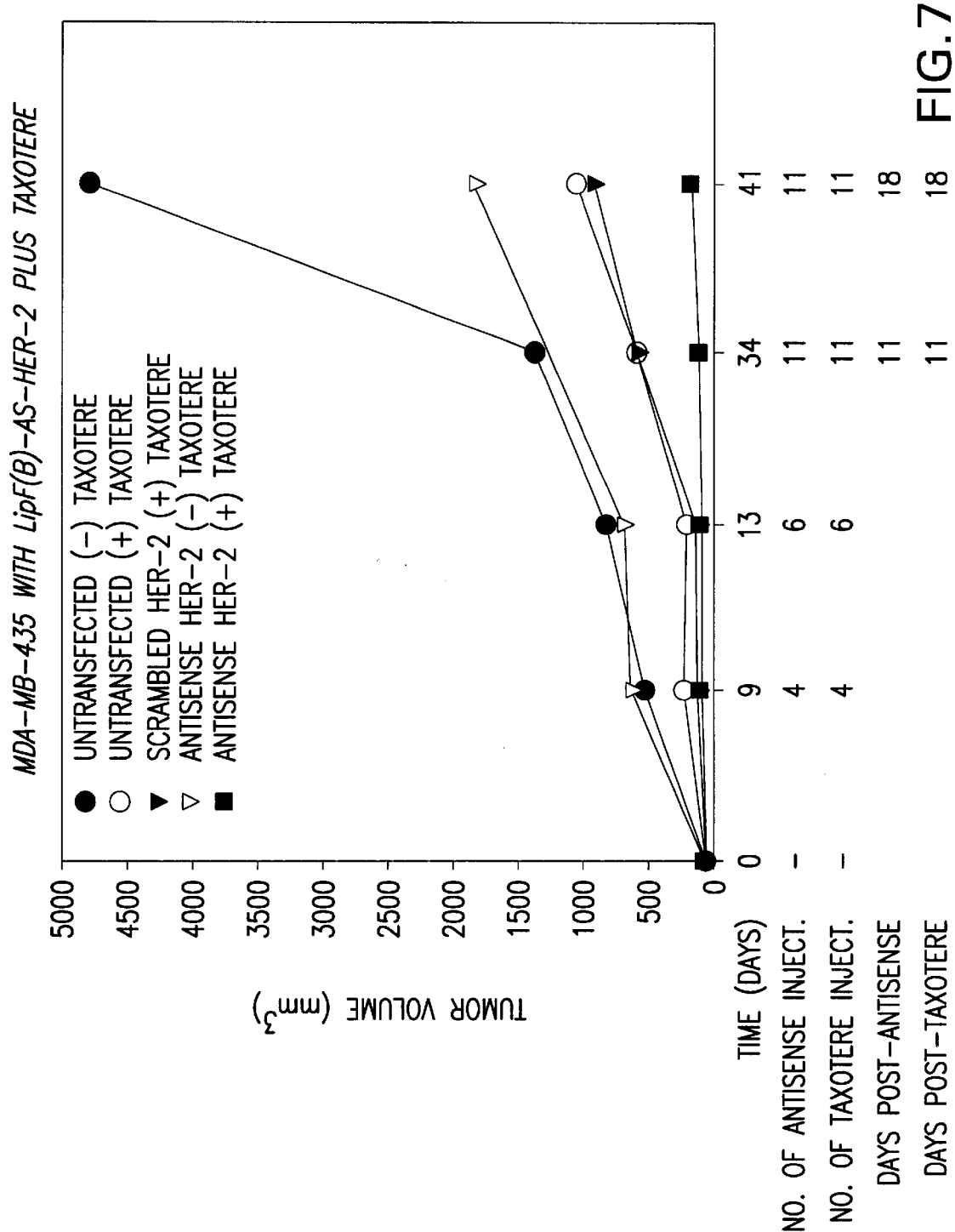
FIG. 7. Curves showing inhibition of tumor growth (MDA-MB-435) in vivo in mice treated with LipF(B)-AS-HER-2 plus Taxotere (docetaxel).

Dramatic growth inhibition of the tumors was evident in the animals receiving the combination of LipF(B)-AS-HER-2 and docetaxel. As shown in FIG. 7, dramatic growth inhibition of the tumors was evident in the animals receiving the combination of LipF(B)-AS-HER-2 and docetaxel. In contrast, only minimal growth inhibition was evident in those mice receiving just AS-HER-2. This difference was statistically significant (p value=0.0009). The difference between either the untreated or docetaxel treated and the combination treated groups was also statistically significant (p value=<0.0001 and p value=0.0004); respectively. Moreover, while there was some docetaxel effect, these tumors began to rapidly increase in size after the cessation of treatment. Therefore, the systemically delivered, targeted liposome delivery of antisense oligonucleotides, in this case AS-HER-2, was clearly able to sensitize these tumors to the chemotherapeutic agent, strongly inhibiting tumor growth almost three weeks after the end of treatment.

EXAMPLE 14

Electron Microscopic Analysis of Ligand-liposome-DNA Complex

Liposomes can be observed under an electron microscope (EM), such as a transmission electron microscope (TEM) with negative staining or a scanning electron microscope (SEM). EM can reveal the structure and size distribution of the liposome complexes. EM can also be used for quality control of liposomal preparation.

In this example, we demonstrate a new, unique transferrin-liposomal structure, one that may account for the stability and efficacy observed with the ligand-liposomal-therapeutic molecule of the invention described in this application.

We observed the ligand-cationic liposomes under Transmission Electron Microscope with negative staining. A copper grid with Formvar and Carbon coating (Electron Microscopy Sciences, Fort Washington, Pa.) was used in the study. Ligand-liposome-pCMVp53 complexes were prepared as described in Examples 6 and 11. One drop of liposome complex was placed on the grid. After 5 minutes, excess liquid was removed by capillary action with filter paper at the edge of the grid. One drop of 4% Uranium Acetate was then added to the grid for negative staining. After 5 minutes, excess liquid was also removed as above. The grid was air dried at room temperature for 15 min before being put into the sample chamber of TEM. The JOEL 1200EX or JOEL 100S were used in the study according to the manufacturer's instruction. Photos were taken at magnitudes of 10–50 k, 60 kVolt. The liposome samples on the grid were prepared, freshly stained and observed within one hour.

Many publications have indicated that cationic liposome-DNA complexes have a diverse structure and size ranging from 100 nm to 1000 nm. In our study, we observed unexpectedly that the ligand-liposome-DNA complexes prepared in accordance with this invention have much smaller size and much more even size distribution. In particular, LipT(A)-p53 complexes have a size ranging from about 30–100 nm in diameter, preferably 35–65 nm (averaging about 50 nm). As the cationic liposome Lip(A) itself has a size of 15–40 nm, averaging 25 nm, when transferrin was complexed with Lip(A), the size did not change appreciably. However, thicker liposomal walls or membranes were observed, indicating that transferrin was complexed onto the liposome membrane. From the enlarged photos we observed an irregular or acentric onion-like structure in the core of the LipT(A)-DNA complex. An intermediate stage of formation of the structure, e.g., an intermediate step in the condensation of the DNA chain by LipT(A), was observed as well. When the incubation time for mixing LipT(A) with DNA was shortened from 15 to 5 minutes, more of this intermediate stage was observed.

Based upon the TEM observations, it appears that the unique structure of the LipT-DNA complex may play in important role in the high gene transfection efficiency observed in vitro and especially in vivo. The acentric onion-like core structure may be formed via the following steps during the formation of the LipT(A)-DNA complex:

Step 1. Several (4–8 or more) Tf-liposomes contact each DNA molecule, attaching to the DNA chain though electrostatic interaction.

Step 2. Each attached Tf-liposome wraps or condenses the DNA chain to form individual lamellar structures along the DNA chain.

Step 3. The lamellar structures condense to form one core lamellar structure. This solid core structure is smaller in size than the sum of 4–8 Tf-liposomes.

Step 4. During the final condensation, a phase transition from lamellar phase to an inverted hexagonal phase may occur, giving rise to the irregular or acentric onion-like structure. The inverted hexagonal ($H_{II}$) phase is believed to be substantially more efficient than the lamellar ($L_{II}$) phase at transfection and may be related to DNA release and delivery (Koltover, I. Science 281:78.1998). Using freeze-fracture electron microscopy, Sternberg et al. (1998) described a "map-pin" structure in DDAB/Chol cationic liposome-DNA complexes that had highest in vivo transfection activity. This high in vivo activity, he believed, is related to small (100–300 nm) stabilized complexes whereas high in vitro activity is associated with hexagonal lipid precipitates. No ultrastructural analysis of ligand-cationic liposome-DNA complexes is available in literature. We believe that in the presence of transferrin or other ligands, the $L_{II}$ to $H_{II}$ transition tends to occur and the formed irregular or acentric onion-like core structure is stabilized by the ligand. As for the mechanism of lamellar-to-inverted-hexagonal phase transition, besides that suggested by Koltover, the ligands may play an important role. Tf attached on liposomal surface or folate linked on the liposomal surface may help or accelerate the phase transition, giving rise to the highly efficient acentric onion-like core structures.

In the preparation conditions disclosed herein, more than 95% of LipT(A)-DNA complexes have the irregular or acentric onion-like core structure. If not for this transition, the condensed lamellar structures in Step 3–4 will preferably form regular or centered onion-like core structure to be stable. This $L_{II}$ to $H_{II}$ transition and Tf-stabilization may account for the unexpectedly high in vivo gene transfection efficiency.

Since the complexation is a four-step process, it is important, when preparing the complex, to incubate for a sufficient period of time between each mixing step, using frequent shaking, to permit the acentric onion-like core structure to form completely. For the preparation procedures disclosed herein, the incubation time should be about 5–15 minutes after each mixing and about 10–30 minutes after mixing with DNA, preferably about 15–30 minutes.

Another unique feature of the liposomes according to the invention is their evenly distributed smaller size (diameter less than about 100 nm, preferably less than about 75 nm, more preferably about 35–65 nm (50 nm average) diameter). To reach the target tumor in vivo, the liposomes must first be resistant to serum and then pass through the blood vessel (capillary) wall. The complexes of the present invention exhibit high resistance to degradation by serum. The permeable size of the capillaries in tumors is usually 50–75 nm; therefore, the complexes can pass through the capillary wall to reach the target.

The TEM structure of LipF(B)-DNA complex is similar to that of LipT(A)-DNA, and this complex has a size range of 30–00 nm, preferably 35–75 nm (average 50 nm) in diameter. The unique irregular or acentric onion-like core structures were also observed. The lamellar-to-inverted-hexagonal phase transition may occur in a similar 4-step process, which accounts for the unexpectedly high in vivo gene transfection efficiency.

The sizes of the complexes consisting of either transferrin (Tf), folate or a single chain scFv fragment of a monoclonal antibody against the transferrin receptor (TfRscFv) as the targeting ligand, cationic liposomes and HER-2 antisense ODN were measured using two different methods. They were first measured by electron microscopy using the procedure described above. They were also measured by Dynamic Light Scattering using a Malvern Zetasizer 3000HSa instrument (Malvem Instruments, UK). Both methods were in agreement, with the sizes of the complexes averaging 100 nm or less, irrespective of the targeting ligand (Tf, folate or TfRscFv) included. Thus, this small size will facilitate penetration of the complex into the tumor via its small capillary blood supply.

EXAMPLE 15

Stability of the Ligand-cationic Liposomes

Stability is an important issue for liposomal pharmaceuticals. Liposome solutions should be stable for an extended period of time after preparation to allow for shipment and storage without substantial loss of their biological/pharmaceutical activities, to be useful as therapeutic agents. In light of the future clinical use of the ligand-liposome-therapeutic molecule complex of this invention, we examined the stability of the ligand-liposomes and the ligand-liposome-DNA complexes.

Lip(A) was prepared in water and stored under nitrogen in the dark at 4° C. for various periods of time, up to 6 months. On the day of the assay, the stored liposomes, as well as freshly prepared Lip(A), was used to make the LipT(A)-pCMVb complex. The complex was then used to transfect JSQ-3 cells using the transfection assay as described in Example 9. No appreciable difference in the level of the transgene expression was observed between the Lip(A) preparations which had been in storage for various lengths of time and the freshly prepared Lip(A). In a separate experiment, a Lip(A) preparation stored for 12 months still retained >90% of its transfection activity. The transferrin solution (5 mg/ml in water) and pCMVb plasmid DNA (0.5–1.0 μg/ml) in 10 mM Tris-HCl, 1 mM EDTA, pH 8.0) were each prepared separately. Folate-liposome complexes were found to have the same degree of stability.

The liposomes, Tf, and plasmid DNA are all individually stable in storage. But, when they are mixed together to form the LipT-DNA complex, the complex is unstable for an extended period of time. For example, the LipT-DNA complex was stable for only a few days. On day 3, only 50% transfection activity remained. For LipF-DNA, only 60% transfection activity remained after 24 hours, with virtually complete loss of activity 3 days after preparation.

Based upon these observations, it appears that the components of the ligand-liposome-therapeutic molecule complexes of this invention can advantageously be provided in kit form. The components can be mixed together sequentially, on the day of use, by first adding the Tf to the liposome, followed by the DNA solution (incubating 10–15 min. between each mixing) then adding dextrose to 5%. The complex should be administered as quickly as practical, preferably within 24 hours, following its preparation.

EXAMPLE 16

In Vivo ODN Stability and Distribution

MDA-Mb-435 xenograft tumors were induced by subcutaneous injection of 2.5–3×10$^6$ cells into the mammary fat pad of female NCR nu/nu athymic nude mice. When the tumors reached approximately 100 mm$^3$ the animals were intravenously injected once, via the tail vein, with 20 nmol of either free As-HER-2 ODN or AS-HER-2 ODN complexed with folate-liposome-2 [(LipF(B)]. The LipF(B)-As-HER-2 ODN complex was prepared for in vivo injection by mixing 300 nmol of LipF(B) (in 100 μl of 5% dextrose) with 20 nmol of ODN (in 100 μl). After 20 min at room temperature, the volume was brought up to 300 μl with 5% Dextrose and injected into the tail vein of the mice.

To evaluate the stability of the ODN alone or in complex with LipF(B) in blood, 100–200 μl of blood was obtained from the mice prior to, and 30 min, 1, 3, 6, 8, 24, 48, 72 hrs after injection and placed in heparinized tubes. Two-thirds of each blood sample was centrifuged at 1,000×g for 7 min. The plasma was removed and 100 μl was incubated with 400 μl of 50% acetonitrile for 30 minutes at room temperature. The mixture was centrifuged at 10,000×g for 20 minutes at 4° C. The supernatant was removed and the ODN precipitated by the addition of 10 volumes of cold 2% LiClO$_4$ in acetone followed by centrifugation at 10,000 ×g for 10 minutes at 4° C. The resulting pellet was dissolved in 100 Ill of water, boiled for 3 minutes and immediately cooled on ice. 10 μl of the ODN was [$^{32}$P] post-labeled as described above. At each time point, the tumor and liver were also excised, rinsed in PBS, minced, flash frozen in liquid nitrogen and stored at −80° C. For the stability assay, the ODN was isolated from tumor and liver as follows: After excision from the animal, the tissue was flash frozen in liquid nitrogen. 100 mg of frozen tissue was crushed using a Bessman Tissue Pulverizer, 400 μl of 50% acetonitrile added, the mixture shaken for 30 min at room temperature and cellular debris removed by centrifugation at 10,000×g for 20 minutes at 4° C. To precipitate the ODN, 10 volumes of cold 2% LiClO$_4$ in acetone was added to the cleared supernatant and centrifuged at 10,000×g for 10 min at 4° C. After washing once with cold acetone, the pellet was dissolved in 100 μl of water, boiled for 3 min. and immediately cooled on ice. The ODN (10 μl) was subsequently [$^{32}$P] post-labeled as described above. The reaction mixtures from the blood and the organs were separated on a 19% polyacrylamide/urea gel and the bands visualized via autoradiography using Biomax MS film (Kodak).

For the ODN distribution assay [$^{35}$S]-labeled ODN (10 μCi, 20 nmol) either alone or in complex with LipF(B) in 300 μl of 5% of dextrose prepared as described above, were intravenously injected into the mice. Samples of blood, plasma, tumor and liver were taken 30 min, 1, 3, 6, 8, 24, 48, 72 hrs after injection. The tumor and liver were flash frozen in liquid nitrogen and crushed while frozen. 100 mg of crushed tissue or 100 μl of plasma were incubated in 2% NaOH solution at 37° C. for 16 hours and subsequently neutralized by the addition of one-fifth the volume of 100 mM ammonium bicarbonate.

The amount of radioactivity in 10 μl of each lysate was determined by liquid scintillation counting using ultima GOLD™XR cocktail (Packard Instruments, Meriden, Conn.).

Results

Stability

Figure 8:
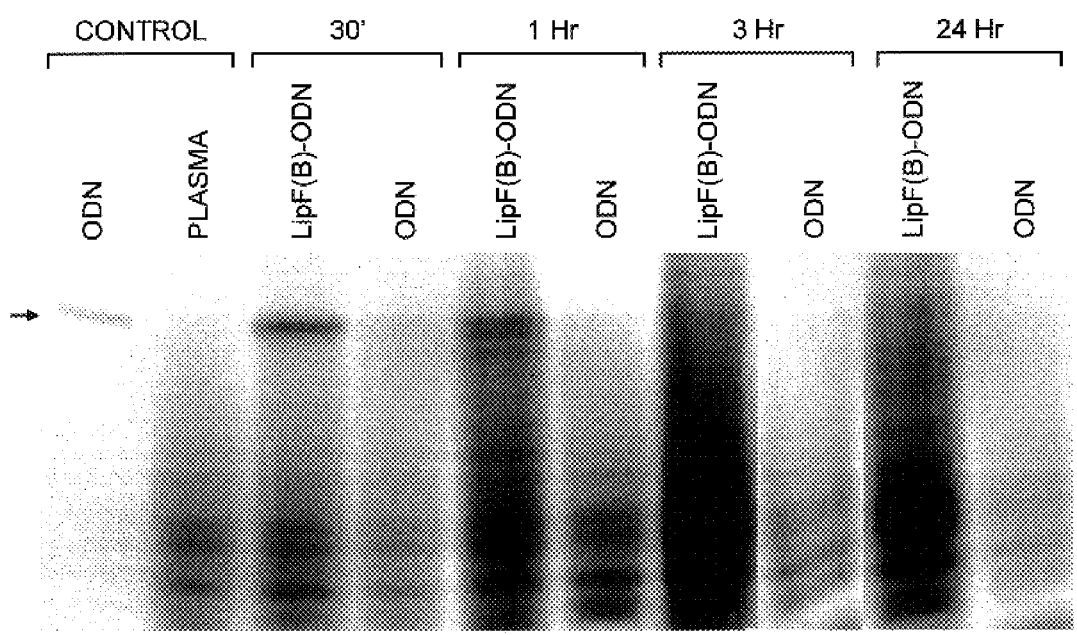
FIG. 8. Autoradiogram showing stability of AS-HER-2 oligonucleotide in blood in both the free state and when complexed with LipF(B).

One of the drawbacks to the use of antisense technology in cancer treatment is the short circulatory half-life of the oligonucleotide. The ability to overcome this problem will have a significant effect on the potential clinical use of antisense ODNs. The data shown in FIG. 8 demonstrates that in complex with LipF(B) the As-HER-2 ODN had significantly increased stability in blood as compared to the free ODN. The arrow indicates the position of the ODN in the gel. Within 30 minutes, approximately 80% of the free ODN had degraded, and was totally gone from the blood stream 1 hour post-injection. In contrast, more than 50% of the complexed ODN was still evident in the blood at this time. Moreover, the presence LipF(B) complexed ODN can still be detected even 24 hours after being injected into the bloodstream of the animal. This improved stability results in an extended time in circulation and consequently an increased opportunity for the complex to reach, and be taken up by, the tumor. Therefore, the use of the ligand-liposome delivery system in antisense therapy is a significant improvement on the current therapeutic use of antisense molecules.

Tumor Distribution

Figure 9:
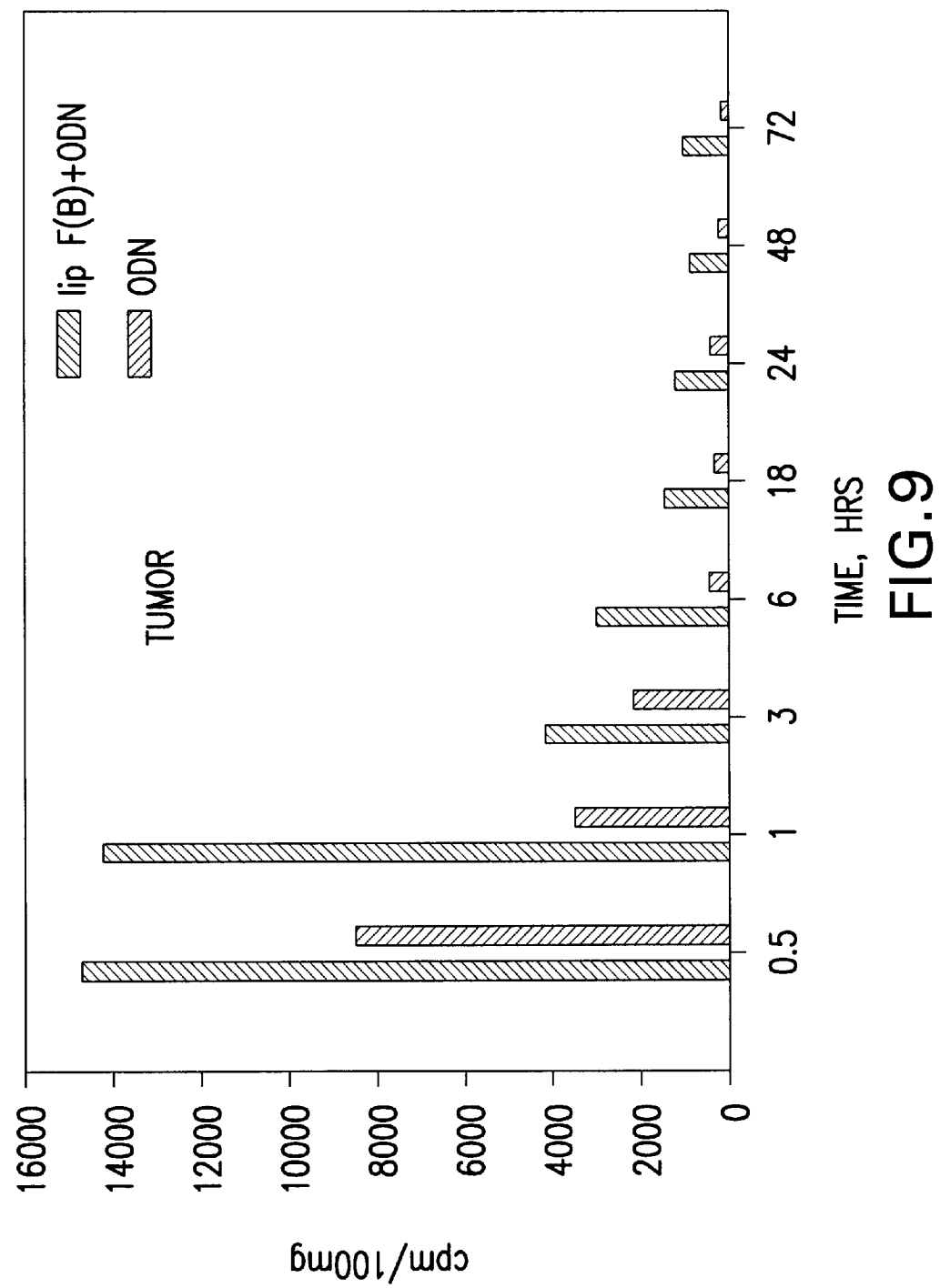
FIG. 9. Histogram showing a time course of the amount of AS-HER-2 oligonucleotide in the tumor in vivo when administered as either the free oligonucleotide or in complex with LipF(B).

We demonstrated above the increased stability of the LipF(B) complexed As-HER-2 ODN in blood after systemic administration. In FIG. 9 we show that the increased circulation time does indeed lead to a significant increase in accumulation in the tumor. This difference, while evident at all time points, was most noticeable at 6 hours post-injection where there was an approximately 7 fold difference between the levels of the free and complexed ODN in the tumor and at one hour (~4 fold difference) where the total amount of ODN in the tumor is maximal. Thus, more efficient delivery of the AS-HER-2 ODN to the tumor will lead to increased AS-ODN effect.

EXAMPLE 17

In Vivo Sensitization to Radiation of Cancer Cells by LipF-AS-HER-2

6.5×10$^6$ EJ tumor cells (human bladder carcinoma) were subcutaneously injected in female athymic (Ncr nu/nu) mice on the lower back near the tail. When tumors reached approximately 100–150 mm$^3$ treatment was begun. The Tf-LipA-AS-HER-2, transferrin targeted Liposome A complexed with antisense HER-2 ODN (phosphorothioated antisense oligonucleotides directed at or near the initiation codon, specifically 5'-TCCATGGTGCTCACT-3', SEQ ID NO:3; synthesized by Midland Certified Reagent Co., Midland, Tex.) (approximately 20 nanomoles of oligonucleotides in 400 μl of total liposome complex), was intratumorally injected 3 times per week, to a total of 19 injections. Two hours after the initial i.v. injection, the animals were secured in a lead restraint so that only the tumor area was exposed to γ-irradiation, and the first fractionated dose of 2.0 Gy of $^{137}$Cs ionizing radiation administered. Thereafter, radiation was administered in 2.0 Gy doses on a daily basis (Monday–Friday) to a total dose of 56 Gy. On Tf-LipA-AS-HER-2 treatment days radiation was given within 2 hours of the injection. For comparison, a group of mice receiving Tf-LipA-AS-HER-2 injection but receiving no radiation, and a group receiving radiation alone, were used as controls. The tumor sizes were measured weekly by the third party from the Georgetown University Animal Facility in a blinded manner. All animal experiments were performed in accordance with Georgetown University institutional guidelines for the care and use of animals.

Figure 10:
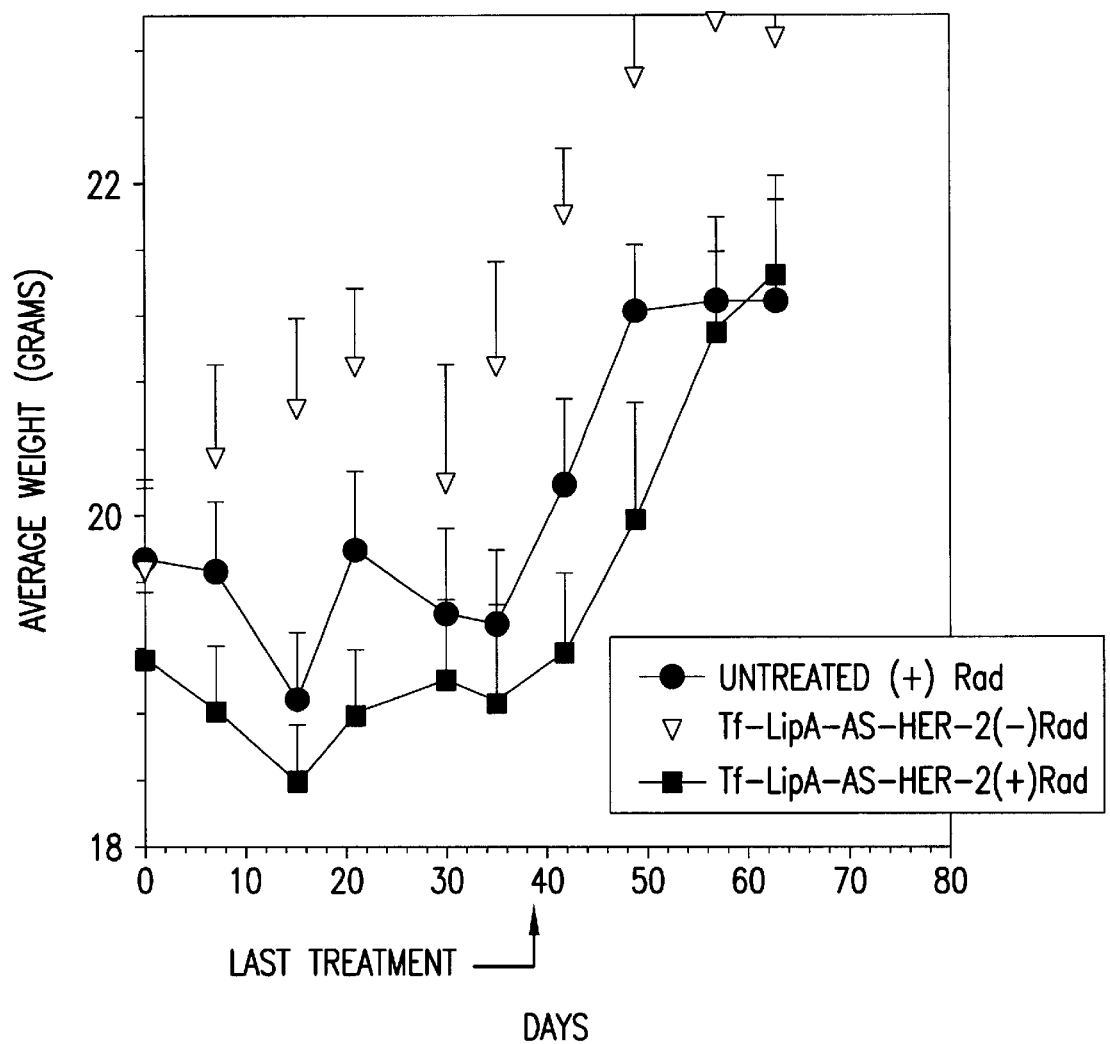
FIG 10. Graph showing time course of body weights of mice treated with radiation, Tf-LipA-AS-HER-2, and radiation plus Tf-LipA-AS-HER-2.

As shown in FIG. 10, there was no significant difference in weight between mice receiving only radiation and mice receiving the combination of Tf-LipA-AS-HER-2 treatment plus radiation. Moreover, mice receiving only the Tf-LipA-AS-HER-2 had the largest increase in weight. These results show that Tf-LipA-AS-HER-2 treatment does not result in toxicity in these animals.

During the treatment period, dramatic growth inhibition of tumors was evident both in mice subjected to the combination of Tf-LipA-AS-HER-2 and radiation, as well as in mice undergoing radiation alone. However, once treatment ended, the combination treatment of Tf-LipA-AS-HER-2 and radiation proved to be more effective than radiation alone in inhibiting tumor growth and size (FIG. 11). This is evident thirty days following the last treatment, when animals treated only with radiation showed a tumor volume of approximately 500 mm$^3$, whereas animals treated with the combination of both Tf-LipA-AS-HER-2 and radiation had tumor volumes of approximately 250 mm$^3$. Thus at this time point, the combination treatment resulted in tumors that were approximately half the size of those treated with radiation alone, showing that the AS-HER-2 combination therapy is twice as efficient as the conventional treatment alone. The targeted liposome delivery of AS-HER-2 was clearly able to sensitize these tumors to radiation, strongly inhibiting tumor growth, even four weeks after the end of treatment.

EXAMPLE 18

In Vivo Treatment of Tumors with Direct Injection

A patient having disease, such as a carcinoma, that can be easily accessed either through direct intratumoral injection or via injection directly to the organ involved or its intra-organ blood supply, can be treated by direct injection of the ligand-liposome-antisense HER-2 ODN (SEQ ID NO:3) complex of this invention in a physiologically compatible buffer. The dosing is preferably begun on day 1 with an initial injection of complex containing HER-2 antisense ODN in an amount ranging from 1 pg/kg to 500 mg/kg body weight into each tumor or organ. Preferably an amount of HER-2 antisense ODN ranging from 0.1 mg/kg to 50 mg/kg body weight will be used.

If the patient is to be treated with the combination of ligand-liposome-antisense HER-2 ODN and radiation, radiotherapy is preferably begun the same day as the ligand-liposome-antisense HER-2 ODN treatment and administered in the standard manner, i.e., approximately 2–5 Gy fractionated doses of radiation administered daily Monday through Friday for a period of about 6 weeks. Dosing with the ligand-liposome-antisense HER-2 ODN is preferably continued three times/week over the period of the 6 weeks of radiotherapy. During the course of the combination treatment the size of the tumors should remain fairly stable or even decrease. Once treatment is finished the tumors are not expected to dramatically increase in size, and may continue to decrease for an extended period of time.

If the patient is to be treated with the combination of ligand-liposome-antisense HER-2 ODN and chemotherapy, chemotherapy is preferably begun the same day as the ligand-liposome-antisense HER-2 ODN and administered in the manner standard for the chemotherapeutic agent used. The ligand-liposome-antisense HER-2 ODN preferably is administered three times/week for the duration of the chemotherapy. The drug of choice is dependent upon the tumor type and organ/tissue involved. For example, the drug docetaxel (Taxotere) is commonly used in the treatment of breast cancer. Docetaxel is administered intravenously on a regimen of either 30–45 mg/m$^2$ bodyweight weekly, or once every three weeks at 60–100 mg/m$^2$. Anywhere from 7 to 200 cycles of drug can be administered. In combination with the ligand-liposome-antisense HER-2 ODN the regimen of choice for this drug is weekly dosing with 30–45 mg/m$^2$ bodyweight. During the course of the combination treatment the size of the tumors should remain fairly stable or even decrease. Once treatment is finished the tumors are not expected to dramatically increase in size, and may continue to decrease for an extended period of time.

EXAMPLE 19

In Vivo Treatment of Tumors with Intravenous Administration

A patient having systemic disease, or disease not easily accessible, will be treated by intravenous administration of the ligand-liposome-antisense HER-2 ODN (SEQ ID NO:3) complex of this invention in a physiologically compatible buffer. The dosing is preferably begun on day 1 with an initial intravenous administration of complex containing HER-2 anti sense ODN in an amount ranging from 1 pg/kg to 500 mg/kg body weight, preferably in an amount ranging from 0.1 mg/kg to 50 mg/kg body weight. The ligand-liposome-antisense HER-2 ODN complex will be administered in combination with standard chemotherapy. Dosing with the complex of this invention will preferably continue three times/week for the duration of the chemotherapeutic regimen. The drug of choice is dependent upon the tumor type and organ/tissue involved. For example, the drug docetaxel (Taxotere) is commonly used in the treatment of breast cancer. Docetaxel is administered intravenously on a regimen of either 30–45 mg/m$^2$ bodyweight weekly, or once every three weeks at 60–100mg/m$^2$. Anywhere from 7 to 200 cycles of drug can be administered. In combination with the ligand-liposome-antisense HER-2 ODN the regimen of choice for this drug is the weekly dosing with 30–45 mg/m$^2$ bodyweight. During the course of the combination treatment the size of the tumors should remain fairly stable or even decrease. Once treatment is finished the tumors are not expected to dramatically increase in size, and should even continue to decrease.

The patient may also be treated with the combination of the systemically delivered ligand-liposome-antisense HER-2 ODN and radiation. In this case radiotherapy preferably is begun the same day as the ligand-liposome-antisense HER-2 ODN treatment and administered in the standard manner, i.e., approximately 2–5 Gy fractionated doses of radiation administered daily Monday through Friday for a period of about 6 weeks. Dosing with the ligand-liposome-antisense HER-2 ODN preferably is continued three times/week over the period of the 6 weeks of radiotherapy. During the course of the combination treatment the size of the tumors should remain fairly stable or even decrease. Once treatment is finished the tumors are not expected to dramatically increase in size, and may continue to decrease for an extended period of time.

Discussion

In our previous studies we examined the relationship between activation of oncogenes and the phenomenon of cellular radiation resistance (Pirollo et al. 1993; Pirollo et al., 1989). We proposed, based upon our findings and those of other researchers, the presence of a signal transduction pathway, analogous to that for cell growth and differentiation, leading to radiation resistance to killing by ionizing radiation (Pirollo et al., 1993). In the studies described above, we present evidence confirming such a pathway. Activation of the raf-1 gene has been shown to be related to radiation resistance in SCCHN and in the non-cancerous skin fibroblasts from a cancer-prone family with Li-Fraumeni syndrome (Kasid et al., 1987; Chang et al., 1987; Pirollo et al., 1989; Kasid et al., 1989). Raf-1 is also known to play a central part in signal transduction via the MAP Kinase pathway (Campbell et al., 1995; Daum et al., 1994). In this Ras/Raf/MER/ERK pathway, a small guanine nucleotide-binding protein links receptor tyrosine kinase activation to a cytosolic protein kinase cascade (Marshall, 1995). The protein-protein interaction between Ras and Raf, through the CRI region on Raf-1 and the effector site of Ras, leads to a partial activation of Raf-1. Full activation of Raf-1 is achieved by another tyrosine kinase generated signal (Marshall, 1995; Fabian et al., 1994) and leads to the phosphorylation and activation of MEK, its only known physiological substrate. This in turn results in the activation of ERK1 and/or ERK2. The substrates for the ERKs in the nucleus are transcription factors, activation of which can set in motion a wide range of events. Raf-1 has also been shown to be a key component in the mammalian response to damage by ultraviolet light (Devary et al., 1992; Radler-Pohl et al., 1993). This "U.V. response" has been proposed to have a protective function, in a manner analogous to that of the bacterial "SOS" system. It was shown by Devary et al. that this pathway originates at the cell membrane and includes activation of Src, and Ha-Ras as well as Raf-1 in a signaling cascade leading to activation of transcription factor AP-1 and nuclear factor kappa B (Devary, 1992).

Protooncogenes and their oncogenic counterparts such as HER-2 (a homologue to an epidermal growth factor receptor) and ras are known to be upstream of raf-1 in the Map Kinase pathway (Daum, 1994; Rapp et al., 1988). The ability, as demonstrated here, of antisense oligonucleotides directed against raf-1 to revert the RR phenotype of cells containing activated ras or overexpressing HER-2 is clear evidence of signaling through raf-1 leading to RR. This is further supported by the ability of antisense ras oligomers to sensitize HER-2 overexpressing SK-OV-3 cells to γ-radiation killing. Although HER-2 is upstream of ras in the signal transduction pathway, ASO directed against HER-2 was also able to affect the RR level of ras transformed T24 cells. These findings may be explained in part by the established interaction between the EGF receptor and adaptor protein/guanine nucleotide exchange factor (Grb2/Sos). Buday and Downward have shown that EGF-induced activation of nucleotide exchange on p21$^{ras}$ proceeds through recruitment of Sos to a complex with the EGF receptor and Grb2 at the plasma membrane and that inhibition of this Grb2-EGFR interaction can inhibit activation of ras (Buday and Downward, 1993). Therefore, it is conceivable that inhibition of the HER-2 protein by ASO can disrupt this interaction, and thus p21$^{ras}$ nucleotide exchange, and interfere with signaling through ras resulting in decreased RR.

Further support for the existence of the pathway leading to RR is found in the work of Morrison et al. (1988) and Haimovitz-Friedman et al. (1991). These investigators found that bFGF, synthesis of which is stimulated in epithelial cells by γ-irradiation (Haimovitz-Friedman et al., 1991) and which in turn activates Raf-1 protein kinase (Buday and Downward, 1993), can protect against radiation-induced cell killing (Haimovitz-Friedman et al., 1991). Our hypothesis of a signal transduction pathway is further confirmed in a recent report by Kasid et at which showed that Raf-1 is phosphorylated/activated after exposure to ionizing radiation by upstream protein tyrosine kinases (Kasid et al., 1996).

These studies, supporting a pathway, with raf-1 as a central element, leading to cellular radioresistance are also clinically significant in a number of ways. Radiation is one of the major forms of adjuvant therapy for various types of cancer. Understanding the molecular mechanisms leading to the failure of a significant fraction of tumors to respond to radiotherapy opens the door to the development of new methods of intervention to radiosensitize tumors, resulting in more effective cancer treatments. In this vein, our use of antisense oligonucleotides to radiosensitize human tumor cells not only establishes the signal transduction pathway, but also demonstrates the potential of these molecules as cancer therapeutic agents showing that ASO directed against a focal point in the pathway can be effective in a number of different tumor types. In a similar way, using mouse m5S cells (Taki et al., 1996) also recently found that ASO against RAD51, a gene involved in recombination and DNA repair, could increase radiosensitivity.

The use of liposome facilitated delivery of the ASO permits significantly lower effective concentrations of oligomers to be used, a step towards eliminating one of the major drawbacks to the clinical use of antisense therapy. The efficacy of ASO is also advantageous for clinical use. At the concentrations employed in these studies, none of the ASOs increased the sensitivity of control radiosensitive cell lines SCC61 and MCF10A, thereby demonstrating that the use of ASO to ameliorate radioresistance is not deleterious to normal tissues thereby strengthening the potential usefulness of ASO in cancer treatment.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Allen T M (1994). *Trends Pharmacol. Sci.* 15:215–220.
Allen T M et al. (1994). *J. Lipos. Res.* 4:1–25.
Allred D C et al. (1992). *J. Clin. Oncol.* 10:599–605.
Ausubel F M et al. (1992). *Current Protocols in Molecular Biology*, (J. Wiley and Sons, N.Y.)
Bishop J M (1991). *Cell* 64:235–248.
Bos J L (1988). *Mutat. Res.* 195:255–271.
Brown D et al. (1989). *Oncogene Res.* 4:243–252.
Buday L and Downward J (1993). *Cell* 73:611–620.
Burris H A (2000). *Semin. Oncol.* 27:19–23.
Campbell J S et al. (l995). *Recent Prog. Horm. Res.* 50:131–59.
Cantley L C et al. (1991). *Cell* 64:281–302.
Chakraborty R et al. (1999). *Biochem. J.* 340:393–396.
Chan S D et al. (1995). *J. Biol. Chem.* 270:22608–22613.
Chang E H et al. (1987). *Science* 237:1036–1039.
Chang E H et al. (1991). *Biochemistry* 30:8283–8286.
Cheng P W (1996). *Hum. Gene Ther.* 7:275–282.
Coussens L (1985). *Science* 230:1132–1139.
Daum G et al. (1994). *Trends Biochem. Sci.* 19:474–480.
Davidson B L et al. (1994). *Exp. Neurol.* 125:258–267.
Devary Y et al. (1992). *Cell* 71:1081–1091.
Fabian J R et al. (1994). *Proc. Natl. Acad. Sci. USA* 91:5982–5986.
FitzGerald T J et al. (1985). *Am. J. Clin. Oncol.* 8:517–522.
Fresta M et al. (1998). *J. Pharm. Sci.* 87:616–625.
Gilewski T et al. (2000). *Cancer Chemother. Pharmacol.* 46 Suppl.:S23–26.
Gokhale P C et al. (1997). *Gene Ther.* 4:1289–1299.
Gregoriadis G and Florence AT (1993). *Drugs* 45:15–28.
Gusterson B A et al. (1992). *J. Clin. Oncol.* 10: 1049–1056.
Haimovitz-Friedman A et al. (1991). *Cancer Res.* 51:2552–2558.
Hunter T (1991). *Cell* 64:249–270.
Janat M F et al. (1994). *Mol. Cell. Diff.* 2:241–253.
Jerian S and Keegan P (1999). *J. Clin. Oncol.* 17:1647–1648.
Kasid U et al. (1987). *Science* 237:1039–1041.
Kasid U N et al. (1989). *Cancer Res.* 49:3396–3400.
Kasid U et al. (1989). Abstract, 5th Annual Meeting on Oncogenes.
Kasid U et al. (1996). *Nature* 382:813–816.
Klapper L N et al. (2000). *Adv. Cancer Res.* 77:25–79.
Lee R J and Low P S (1994). *J. Biol. Chem.* 269:3198–3204.
Ling C C and Endlich B (1989). *Radiat. Res.* 120:267–279.
Marshall C J (1995). *Cell* 80:179–185.
McGrew B R et al. (1992). *Oncogene* 7:33–42.
McKenna W G et al. (1990). *Cancer Res.* 50:97–102.
McNeil C (2000). *J. Natl. Cancer Inst.* 92:683–684.
Mercola D and Cohen J S (1995). *Cancer Gene Ther.* 47–59.
Meyer O et al. (1998). *J. Biol. Chem.* 273:15621–15627.
Mori A et al. (1991). *FEBS Lett.* 284:263–266.
Morrison D K (1990). *Cancer Cells* 2:377–382.
Morrison D K et al. (1988). *Proc. Natl. Acad. Sci. USA* 85:8855–8859.
Muss H B et al (1994). *N. Engl. J. Med.* 330:1260–1266.
Pagnan G et al. (2000). *J. Natl. Cancer Inst.* 92:253–261.
Pegram M D et al. (1993). *Proc. 84th Ann. Mtg. of AACR*, Orlando, 19–22 May 1993 34, p26 (Abstract).
Pegram M D and Slamon D J (1999). *Semin. Oncol.* 26:89–95.
Pirollo K F et al. (1989). *Int. J. Radiat. Biol.* 55:783–796.
Pirollo K F et al. (1993). *Radiat. Res.* 135:234–243.
Pirollo K F et al. (1997). *Biochem. Biophys. Res. Commun.* 230:196–201.
Plenat F (1996). *Mol. Med. Today* 2:250–257.
Radler-Pohl A et al. (1993). *EMBO J.* 12:1005–1012.
Rapp U R et a]. (1988). *In The Oncogene Handbook* (T. Curran, J. E. P. Reddy and A. Skala, Eds.), pp. 213–252. Elsevier, Amsterdam.
Scanlon K J et al. (1995). *FASEB J.* 9:1288–1296.
Schaller G et al. (1999). *J. Cancer Res. Clin. Oncol.* 125:520–524.

Semple S C et al. (2000). *Methods Enzymol.* 313:322–341.
Shak S (1999). *Semin. Oncol.* 26:71–77.
Sklar M D et al. (1986). *Int. J. Radiat. Oncol. Biol. Phys.* 2:190–191.
Sklar M D (1988). *Science* 239:645–647.
Smith M R et al. (1986). *Nature* 320:540–543.
Stein C A et al. (1988). *Nucl. Acids Res.* 16:3209–3221.
Sternberg B et al. (1998). *Biochim. Biophys. Acta* 1375:23–35.
Suzuki K et al. (1992). *Radiat. Res.* 129:157–162.
Tabin C J. et al. (1982). *Nature* 300:143–149.
Taki T et al. (1996). *Biochem. Biophys. Res. Commun.* 223:434–438.
Tidd D M (1990). *Anticancer Res.* 10:1169–1182.
Tsai C-M et al. (1993). *J. Natl. Cancer. Inst.* 85:897–901.
Ts'o P O P et al. (1992). *Ann. N.Y Acad Sci.* 660:159–177.
Tzahar E and Yarden Y (1998). *Biochim. Biophys. Acta* 1377:M25–M37.
Uhlmann E and Peyman A (1990). *Chem. Rev.* 90:544–584.
Van Diest P J. et al. (1992). *Pathol. Res. Pract.* 188:344–349.
Weichselbaum R R et al. (1986). *Proc. Natl. Acad. Sci. USA* 83:2684–2688.
Weichselbaum R R et al. (1988). *Int. J. Radiat. Oncol. Biol. Phys.* 15:575–579.
Weinstein I B (1988). *Mutat. Res.* 202:413 420.
Wright C et al. (1992). *Br. J. Cancer* 65:271–274.
Yu Z et al. (1989). *J. Exp. Pathol* 4:97–108.

---

What is claimed is:

1. A therapeutic agent for treating diseases associated with an increase in radiation resistance or drug resistance of a cell, said agent comprising an isolated sequence comprising 5'-TCCATGGTGCTCACT-3' (SEQ ID NO:3) wherein said agent reduces radiation resistance or drug resistance of said cell.

2. The therapeutic agent of claim 1 wherein said agent reduces drug resistance of said cell and further wherein said drug resistance is a resistance to a chemotherapeutic agent.

3. A method for reducing radiation or drug resistance of a human cell which does not overexpress HER-2, said method comprising introducing into said cell an antisense nucleic acid comprising a segment complementary to HER-2 in an amount effective to reduce said radiation or drug resistance.

4. The method of claim 3 wherein said cell is a carcinoma cell selected from the group consisting of breast, bladder, prostate, head, neck, lung, colon, pancreas, cervical, ovarian, melanoma and stomach carcinoma cells.

5. The method of claim 3 wherein said antisense nucleic acid is introduced by association with a targeted liposome.

6. The method of claim 5, wherein said targeted liposome comprises a complex of a ligand and a liposome comprising a mixture of a cationic lipid and a neutral lipid.

7. The method of claim 6, wherein said liposome comprises a mixture of dioleoyltrimethylammoniumpropane (DOTAP) and dioleoylphosphatidylethanolamine (DOPE).

8. The method of claim 6, wherein said ligand comprises folate or transferrin.

9. The method of claim 3 wherein said antisense nucleic acid comprises SEQ ID NO:3.

10. A method for treating a person with a disease wherein said person is resistant to radiation or drug treatment of said disease, wherein resistance to said radiation or drug treatment is not a result of overexpression of HER-2, said method comprising administering to said person an antisense nucleic acid comprising a segment complementary to HER-2 in an amount effective to decrease said resistance to radiation or drug treatment.

11. The method of claim 10 wherein said resistance to radiation or drug treatment results from a mutation in or overexpression of a gene selected from the group consisting of sis (PDGF-$\beta$); trk; met; src; mos; protein kinase C $\beta$-1; ets-1; raf-1; Ha-ras; c-Fos; c-Jun; c-myc; Shc; Grb2; Sos; PLC$_\gamma$; and a gene encoding ERK1, ERK2, MEKK, MEK1, MEK2, MAPK, SAPK, MAP2, MAP4, TNF-$\alpha$ receptor, EGF receptor, PKC-$\alpha$, PC-PLC, PKC-$\epsilon$, an RTK, a TCR-CD3, an STMR, a PTKs, or a G protein.

12. The method of claim 11 wherein said gene is Ha-ras.

13. The method of claim 11 wherein said gene is raf-1.

14. The method of claim 10 wherein said antisense nucleic acid comprises SEQ ID NO:3.

15. The method of claim 10, wherein said antisense nucleic acid is administered via a targeted liposome which comprises a complex of a ligand and a liposome comprising a mixture of a cationic lipid and a neutral lipid.

16. The method of claim 15, wherein said liposome comprises a mixture of dioleoyltrimethylammoniumpropane (DOTAP) and dioleoylphosphatidylethanolamine (DOPE).

17. The method of claim 15, wherein said ligand comprises folate or transferrin.

18. A method for reducing radiation or drug resistance of a human cell which overexpresses HER-2, said method comprising introducing into said cell an antisense nucleic acid comprising a segment complementary to HER-2 in an amount effective to reduce said radiation or drug resistance.

19. The method of claim 18 wherein said cell is a carcinoma cell selected from the group consisting of breast, bladder, prostate, head and neck, lung, colon, pancreas, cervical, ovarian, melanoma and stomach carcinoma cells.

20. The method of claim 18 wherein said antisense nucleic acid is introduced by association with a targeted liposome.

21. The method of claim 20, wherein said targeted liposome comprises a complex of a ligand and a liposome comprising a mixture of a cationic lipid and a neutral lipid.

22. The method of claim 21, wherein said liposome comprises a mixture of dioleoyltrimethylammoniumpropane (DOTAP) and dioleoylphosphatidylethanolamine (DOPE).

23. The method of claim 21, wherein said ligand comprises folate or transferrin.

24. The method of claim 18 wherein said antisense nucleic acid comprises SEQ ID NO:3.

25. A method for treating a person with a disease wherein said person is resistant to radiation or drug treatment of said disease, wherein resistance to said radiation or drug treatment is a result of overexpression of HER-2, said method comprising administering to said person an antisense nucleic acid comprising a segment complementary to HER-2 in an amount effective to decrease said resistance to radiation or drug treatment.

26. The method of claim 25 wherein said resistance to radiation or drug treatment results from a mutation in or overexpression of a gene selected from the group consisting of sis (PDGF-$\beta$); trk; met; src; mos; protein kinase C $\beta$-1; ets-1; raf-1; Ha-ras; c-Fos; c-Jun; c-myc; Shc; Grb2; Sos; PLC$_\gamma$; and a gene encoding ERK1, ERK2, MEKK, MEK1, MEK2, MAPK, SAPK, MAP2, MAP4, TNF-$\alpha$ receptor, EGF receptor, PKC-$\alpha$, PC-PLC, PKC-$\epsilon$, an RTK, a TCR-CD3, an STMR, a PTKs, or a G protein.

27. The method of claim 26 wherein said gene is Ha-ras.

28. The method of claim 26 wherein said gene is raf-1.

29. The method of claim 25 wherein said antisense nucleic acid comprises SEQ ID NO:3.

30. The method of claim 25, wherein said antisense nucleic acid is administered via a targeted liposome which comprises a complex of a ligand and a liposome comprising a mixture of a cationic lipid and a neutral lipid.

31. The method of claim 30, wherein said liposome comprises a mixture of dioleoyltrimethylammoniumpropane (DOTAP) and dioleoylphosphatidylethanolamine (Dope).

32. The method of claim 30, wherein said ligand comprises folate or transferrin.

* * * * *